US 012148162B2

(12) United States Patent
Gardella et al.

(10) Patent No.: US 12,148,162 B2
(45) Date of Patent: Nov. 19, 2024

(54) SYSTEMS AND METHODS FOR DETECTING CARDIOVASCULAR ANOMALIES USING SPATIOTEMPORAL NEURAL NETWORKS

(71) Applicant: BrightHeart SAS, Paris (FR)

(72) Inventors: Christophe Gardella, Paris (FR); Valentin Thorey, Paris (FR); Eric Askinazi, Paris (FR); Cécile Dupont, Paris (FR)

(73) Assignee: BrightHeart SAS, Paris (FR)

( * ) Notice: Subject to any disclaimer, the term of this patent is extended or adjusted under 35 U.S.C. 154(b) by 0 days.

(21) Appl. No.: 18/412,325

(22) Filed: Jan. 12, 2024

(65) Prior Publication Data

US 2024/0281971 A1 Aug. 22, 2024

Related U.S. Application Data

(63) Continuation-in-part of application No. 18/183,942, filed on Mar. 14, 2023, now Pat. No. 11,875,507.

(30) Foreign Application Priority Data

Feb. 22, 2023 (EP) .................................. 23305236

(51) Int. Cl.
*G06K 9/00* (2022.01)
*G06T 7/00* (2017.01)
*G16H 15/00* (2018.01)

(52) U.S. Cl.
CPC .......... *G06T 7/0014* (2013.01); *G16H 15/00* (2018.01); *G06T 2200/24* (2013.01);
(Continued)

(58) Field of Classification Search
None
See application file for complete search history.

(56) References Cited

U.S. PATENT DOCUMENTS 7,672,491 B2 3/2010 Krishnan et al.
11,478,222 B2 10/2022 Shiran et al.
(Continued)

FOREIGN PATENT DOCUMENTS

CN 114469176 A 5/2022
CN 114677754 A 6/2022
(Continued)

OTHER PUBLICATIONS

Abuhamad A., et al., "Obstetric and Gynecologic Ultrasound Curriculum and Competency Assessment in Residency Training Programs: Consensus Report: Obstetric and Gynecologic Ultrasound Training," Journal of Ultrasound in Medicine, vol. 37(1):19-50, DOI:10.1002/jum.14519 (Jan. 2018).
(Continued)

*Primary Examiner* — Wei Wen Yang
(74) *Attorney, Agent, or Firm* — Greenberg Traurig, LLP; Christopher C. Bolten; Robert D. Ward

(57) ABSTRACT

Systems and methods are provided for processing image data generated by a medical imaging device such as an ultrasound or echocardiogram device and processing the image data using artificial intelligence and machine learning to determine a presence of one or more congenital heart defects (CHDs) and/or other cardiovascular anomalies in the image data and/or to determine key-point and/or contour detection. The image processing system may be used to detect CHDs and/or other cardiovascular anomalies in a fetus. The image data may be processed using a spatiotemporal convolutional neural network (CNN). The spatiotemporal CNN may include a spatial CNN for image recognition and a temporal CNN for processing optical flow data based on the image data. The outputs of the spatial CNN and the temporal CNN may be fused (e.g., using late fusion) to
(Continued)

generate a likelihood of CHDs and/or other cardiovascular anomalies.

28 Claims, 9 Drawing Sheets

(52) U.S. Cl.
CPC .............. *G06T 2207/10016* (2013.01); *G06T 2207/10132* (2013.01); *G06T 2207/20081* (2013.01); *G06T 2207/20084* (2013.01); *G06T 2207/30044* (2013.01); *G06T 2207/30048* (2013.01); *G06T 2207/30101* (2013.01)

(56) References Cited

U.S. PATENT DOCUMENTS

| | | | |
|---|---|---|---|
| 11,488,298 | B2 | 11/2022 | Annangi et al. |
| 11,517,290 | B2 | 12/2022 | Aase et al. |
| 11,861,838 | B1 | 1/2024 | Gardella et al. |
| 11,869,188 | B1 | 1/2024 | Levy et al. |
| 11,875,507 | B1 | 1/2024 | Gardella et al. |
| 2005/0004465 | A1 | 1/2005 | Abuhamad |
| 2005/0251013 | A1 | 11/2005 | Krishnan et al. |
| 2005/0251036 | A1 | 11/2005 | Abuhamad |
| 2014/0050384 | A1 | 2/2014 | Schmidt et al. |
| 2017/0337731 | A1 | 11/2017 | Jago et al. |
| 2018/0206819 | A1 | 7/2018 | Saarinen et al. |
| 2020/0155114 | A1 | 5/2020 | Park et al. |
| 2020/0214618 | A1 | 7/2020 | Vullings |
| 2020/0345261 | A1 | 11/2020 | Haeusser et al. |
| 2021/0034587 | A1 | 2/2021 | Arye et al. |
| 2021/0150693 | A1 | 5/2021 | Fornwalt et al. |
| 2021/0202069 | A1 | 7/2021 | Van Der Veen et al. |
| 2021/0280298 | A1 | 9/2021 | Samset et al. |
| 2021/0319558 | A1 | 10/2021 | Min et al. |
| 2021/0345987 | A1 | 11/2021 | Ciofolo-Veit et al. |
| 2022/0012875 | A1 | 1/2022 | Arnaout |
| 2022/0142609 | A1 | 5/2022 | Yeo et al. |
| 2022/0361799 | A1 | 11/2022 | Hong et al. |
| 2023/0064623 | A1 | 3/2023 | Krishnan et al. |
| 2023/0135046 | A1 | 5/2023 | Liu et al. |

FOREIGN PATENT DOCUMENTS

| | | |
|---|---|---|
| CN | 115424335 A | 12/2022 |
| EP | 3964136 A1 | 3/2022 |
| EP | 4144301 A1 | 3/2023 |
| WO | WO-2022265345 A1 * | 12/2022 |

OTHER PUBLICATIONS

Activity recognition, Wikipedia the Free Encyclopedia, retrieved from the internet URL: https://en.wikipedia.org/wiki/Activity_recognition, 12 pages (2018).
"AIUM Practice Guideline for the Performance of Fetal Echocardiography," Fetal Echocardiography Task Force; American Institute of Ultrasound in Medicine Clinical Standards Committee; American College of Obstetricians and Gynecologists; Society for Maternal-fetal Medicine, Journal of Ultrasound in Medicine, vol. 30(1):27-136, doi: 10.7863/jum.2011.30.1.127 (Jan. 2011).
AIUM-ACR-ACOG-SMFM-SRU Practice Parameter for the Performance of Standard Diagnostic Obstetric Ultrasound Examination, J. Ultrasound Med., 37:E13-E24 (2018).
Alom, et al., The History Began from AlexNet: A Comprehensive Survey on Deep Learning Approaches, retrieved from the internet URL: https://arxiv.org/abs/1803.01164, 39 pages (2018).
Arnaout, et al., An Ensemble of Neural Networks Provides Expert-Level Prenatal Detection of Complex Congenital Heart Disease, Nature Medicine, 27(5):882-891 (May 2021).
Arth et al., "Inpatient Hospitalization Costs Associated with Birth Defects Among Persons of All Ages-United States, 2013," MMWR Morbidity and Mortality Weekly Report, vol. 66(2):41-46, DOI:10.15585/mmwr.mm6602a1. (Jan. 20, 2017).
Berghella V., et al., "Accuracy of Prenatal Diagnosis of Congenital Heart Defects," Fetal Diagnosis and Therapy, vol. 16(6):407-412, DOI:10.1159/000053949. (Mar. 2001).
Bjornard K., et al., "Patterns in the Prevalence of Congenital Heart Defects, Metropolitan Atlanta, 1978 to 2005," Birth Defects Research. (Part A): Clinical and Molecular Teratology, vol. 97(2):87-94, doi:10.1002/bdra.23111 (Feb. 2013).
Bonnet D., et al., "Detection of Transposition of the Great Arteries in Fetuses Reduces Neonatal Morbidity and Mortality," Circulation, vol. 99(7):916-918, DOI:10.1161/01.cir.99.7.916. (Feb. 1999).
Cardinal M., et al., "Incremental Detection of Severe Congenital Heart Disease by Fetal Echocardiography Following a Normal Second Trimester Ultrasound Scan in Québec, Canada," Circulation. Cardiovascular Imaging, vol. 15(4):240-248, doi:10.1161/CIRCIMAGING.121.013796 (Apr. 2022).
Carreira, et al., Quo Vadis, Action Recognition? A New Model and the Kinetics Dataset, retrieved from the internet URL: https://arxiv.org/abs/1705.07750, 10 pages (2018).
Carvalho, et al., ISUOG Practice Guidelines (updated): sonographic screening examination of the fetal heart, Ultrasound Obstet. Gynecol., 41:348-359 (2013).
Carvalho J.S., et al., "ISUOG Practice Guidelines (updated): fetal cardiac screening," Ultrasound Obstet Gynecol, vol. 61(6):788-803, DOI:10.1002/uog.26224. (Jun. 2023).
Centers for Disease Control and Prevention (CDC), "Racial Differences by Gestational Age in Neonatal Deaths Attributable to Congenital Heart Defects—United States, 2003-2006," Morbidity and Mortality Weekly Report (MMWR), vol. 59(37):1208-1211 (Sep. 2010).
Cluster, Construct Clusters from Gaussian Mixture Distribution, retrieved from the internet URL: https://www.mathworks.com/help/stats/gmdistribution.cluster.html, 6 pages, retrieved on Apr. 13, 2023.
Cluster Gaussian Mixture Data Using Hard Clustering, retrieved from the internet URL: https://www.mathworks.com/help/stats/cluster-data-from-mixture-of-gaussian-distributions.html, retrieved on Apr. 13, 2023, 6 pages.
Cluster Gaussian Mixture Data Using Soft Clustering, retrieved from the internet URL: https://www.mathworks.com/help/stats/cluster-gaussian-mixture-data-using-soft-clustering.html, retrieved on Apr. 13, 2023, 5 pages.
Create Gaussian Mixture Model, retrieved from the internet URL: https://www.mathworks.com/help/stats/gmdistribution.html#mw_132ef7d2-0aa5-498f-bd6e-824f3edc8567, retrieved on Apr. 13, 2023, 8 pages.
Data Sets, UCF101—Action Recognition Data Set, UCF Center for Research in Computer Vision, 6 pages (2012).
Day, et al., Artificial Intelligence, Fetal Echocardiograhy, and Congenital Heart Disease, Prenatal Diagnosis, 41 (6):733-42 (May 2021).
Donofrio, et al., Diagnosis and Treatment of Fetal Cardiac Disease, A Scientific Statement From the American Heart Association, Circulation, 129(21):2183-242 (May 2014).
Eckersley L., et al., "Timing of Diagnosis Affects Mortality in Critical Congenital Heart Disease," Archives of Disease in Childhood, vol. 101(6):516-520, doi:10.1136/archdischild-2014-307691 (Jun. 2016).
Espinoza J., et al., "The Role of the Sagittal View of the Ductal Arch in Identification of Fetuses With Conotruncal Anomalies Using 4-Dimensional Ultrasonography," J Ultrasound Med., vol. 26(9):1181-1188, doi: 10.7863/jum.2007.26.9.1181 (Sep. 2007).
Feichtenhofer, et al., Convolutional Two-Stream Network Fusion for Video Action Recognition, retrieved from the internet URL: https://arxiv.org/abs/1604.06573, 9 pages (2016).
Feichtenhofer, et al., Slow Fast Networks for Video Recognition, retrieved from the internet URL: hhttps://arxiv.org/abs/1812.03982, 10 pages (2019).
Feichtenhofer, et al., Spatiotemporal Residual Networks for Video Action Recognition, retrieved from the internet URL: https://arxiv.org/abs/1611.02155, 9 pages (2016).

(56) References Cited

OTHER PUBLICATIONS

Fitgmdist, Fit Gaussian Mixture Model to Data, MATLAB fitgmdist, retrieved from the internet URL: https://www.mathworks.com/help/stats/fitgmdist.html, retrieved on Apr. 13, 2023, 17 pages.
Friedberg M.K., et al., "Prenatal Detection of Congenital Heart Disease," The Journal of Pediatrics, vol. 155 (1):26-31, doi:10.1016/j.jpeds.2009.01.050 (Jul. 2009).
Gao, et al., Fast Video Multi-Style Transfer, IEEE Winter Conference on Applications of Computer Vision (WACV), pp. 3222-3230 (2020).
Gatys, et al., A Neural Algorithm of Artistic Style, retrieved from the internet URL: https://arxiv.org/abs/1508.06576, 16 pages (2015).
Gkioxari, et al., Finding Action Tubes, retrieved from internet URL: https://arxiv.org/abs/1411.6031, 10 pages (Nov. 2014).
Goodale, et al., Separate Visual Pathways for Perception and Action, Trends in Neurosciences, 15(1):20-25 (Jan. 1992).
Grandjean, et al., The performance of routine ultrasonographic screening of pregnancies in the Eurofetus Study, American Journal of Obstetrics and Gynecology, 181(2):446-454 (Aug. 1999).
He, et al., Deep Residual Learning for Image Recognition, In Proceedings of the IEEE Conference on Computer Vision and Pattern Recognition, pp. 770-778 (2016).
He R., et al., "Examining Contributing Factors to Accuracy of Fetal Echocardiography in Prenatal Diagnosis of Congenital Heart Disease," Journal of the American College of Cardiology, vol. 77(18):502, DOI:10.1016/S0735-1097 (21)01861-1. (May 2021).
HMDB: A Large Human Motion Database, Serre Lab, retrieved from the internet URL: https://serre-lab.clps.brown.edu/resource/hmdb-a-large-human-motion-database/, accessed on Mar. 23, 2023, 6 pages.
Hoffman J.I.E., et al., "The Incidence of Congenital Heart Disease," Journal of the American College of Cardiology, vol. 39(12):1890-1900, doi:10.1016/S0735-1097(02)01886-7 (Jun. 19, 2002).
Holland B.J., et al., "Prenatal diagnosis of critical congenital heart disease reduces risk of death from cardiovascular compromise prior to planned neonatal cardiac surgery: a meta-analysis," Ultrasound Obstet Gynecol, vol. 45 (6):631-638, DOI:10.1002/uog.14882. (Jun. 2015).
Howard, et al., Improving Ultrasound Video Classification: an Evaluation of Novel Deep Learning Methods in Echocardiography, Journal of Medical Artificial Intelligence, 14 pages (Mar. 2020).
Huang, Real-Time Neural Style Transfer for Videos, IEEE Conference on Computer Vision and Pattern Recognition (CVPR), 9 pages (2017).
Image Gradient, Wikipedia the Free Encyclopedia, retrieved from the internet URL: https://en.wikipedia.org/wiki/Image_gradient, accessed on Mar. 23, 2023, 3 pages.
Ioffe, et al., Batch Normalization: Accelerating Deep Network Training by Reducing Internal Covariate Shift, retrieved from internet URL: https://arxiv.org/abs/1502.03167, 11 pages (2015).
Israel S.W., et al., "Improvement in Antenatal Diagnosis of Critical Congenital Heart Disease Implications for Postnatal Care and Screening," Fetal Diagnosis and Therapy, vol. 30(3):180-183, DOI:10.1159/000327148. (Apr. 2011).
Ji, et al., 3D Convolutional Neural Networks for Human Action Recognition, IEEE Transactions on Pattern Analysis and Machine Intelligence, 35(1), 8 pages (Jan. 2013).
Krizhevsky, et al., ImageNet Classification with Deep Convolutional Neural Networks, Communications of the ACM, 60(6):84-90 (Jun. 2017).
Kuehl, et al., Failure to Diagnose Congenital Heart Disease in Infancy, Pediatrics, 103(4):743-747 (Apr. 1999).
Landis B.J., et al., "Prenatal Diagnosis of Congenital Heart Disease and Birth Outcomes," Pediatric Cardiology, vol. 34(3):597-605, doi:10.1007/s00246-012-0504-4. (Mar. 2013).
Levy, et al., Fetal Echocardiography: 5-4-3-2-1, The Levy-Stos Method, Gynecologie Obstetrique Pratique, No. 309 (Nov. 2018) (w-English Translation).
Levy, et al., Improved Prenatal Detection of Congenital Heart Disease in an Integrated Health Care System, Pediatr. Cardiol., 34:670-679 (Mar. 2013).
U.S. Appl. No. 18/183,937 / U.S. Pat. No. 11,869,188, filed Mar. 14, 2023 / Jan. 9, 2024.
U.S. Appl. No. 18/183,942 / U.S. Pat. No. 11,875,507, filed Mar. 14, 2023 / Jan. 16, 2024.
U.S. Appl. No. 18/330,819 / U.S. Pat. No. 11,861,838, filed Jun. 7, 2023 / Jan. 2, 2024.
U.S. Appl. No. 18/406,446, filed Jan. 8, 2024.
Liu, et al., Generalize Ultrasound Image Segmentation via Instant and Plug Play Style Transfer, retrieved from internet URL: https://arxiv.org/abs/2101.03711, 5 pages (2021).
Liu, et al., Remove Appearance Shift for Ultrasound Image Segmentation via Fast and Universal Style Transfer, retrieved from internet URL: https://arxiv.org/abs/2002.05844, 6 pages (2020).
Mai C.T., et al., "National Population-based Estimates for Major Birth Defects, 2010-2014," Birth Defects Research, vol. 111(18):420-1435, doi:10.1002/bdr2.1589 (Nov. 2019).
Mamasoula C., et al., "Maternal age and the prevalence of congenital heart defects in Europe, 1995-2015: A register-based study," Birth Defects Research, vol. 115(6):583-594, Doi:10.1002/bdr2.2152. (Apr. 2023).
McMahon C.J., et al., "Paediatric and adult congenital cardiology education and training in Europe," Cardiol Young, vol. 32(12):1966-1983, DOI:10.1017/S104795112100528X. (Dec. 2022).
Moon-Grady A., et al., "Can a Complete Fetal Echocardiogram be Performed at 12 to 16 weeks' Gestation?" Journal of the American Society of Echocardiography: official publication of the American Society of Echocardiography, vol. 25(12):1342-1352, DOI:10.1016/j.echo.2012.09.003. (Dec. 2012).
Mozumdar N., et al., "Diagnostic Accuracy of Fetal Echocardiography in Congenital Heart Disease," Journal of the American Society of Echocardiography, vol. 33(11):1384-1390, DOI:10.1016/j.echo.2020.06.017. (Nov. 2020).
Nayak K., et al., "Evaluation of Fetal Echocardiography as a Routine Antenatal Screening Tool for Detection of Congenital Heart Disease," Cardiovascular Diagnosis and Therapy, vol. 6(1):44-49, doi:10.3978/j.issn.2223-3652.2015.12.01 (Feb. 2016).
Olney R.S., et al., "Detection of Critical Congenital Heart Defects: Review of Contributions from Prenatal and Newborn Screening," Seminars in Perinatology, vol. 39(3):230-237, doi:10.1053/j.semperi.2015.03.007 (Apr. 2015).
Optical flow, Wikipedia The Free Encyclopedia, retrieved from the internet URL: https://en.wikipedia.org/wiki/Optical_flow, accessed on Mar. 23, 2023, 6 pages.
Oster M.E., et al., "Temporal Trends in Survival Among Infants With Critical Congenital Heart Defects," Pediatrics, vol. 131(5):e1502-e1508, doi:10.1542/peds.2012-3435 (May 2013).
Ouyang, et al., Interpretable AI for Beat-to-Beat Cardiac Function Assessment, Stanford University, 23 pages (2019).
Pan, et al., An Improved Two-stream Inflated 3D ConvNet for Abnormal Behavior Detection, Intelligent Automation and Soft Computing, 29(3):673-688 (Jan. 2021).
Peiris V., et al., "Association of Socioeconomic Position and Medical Insurance With Fetal Diagnosis of Critical Congenital Heart Disease," Circulation. Cardiovascular quality and outcomes, vol. 2(4):354-360, DOI:10.1161/CIRCOUTCOMES.108.802868. (Jul. 2009).
Pinto N.M., et al., "Barriers to Prenatal Detection of Congenital Heart Disease: a Population-based Study," Ultrasound in Obstetrics Gynecology, vol. 40(4):418-425, doi:10.1002/uog.10116 (Oct. 2012).
Pradat P., et al., "The Epidemiology of Cardiovascular Defects, Part I: A Study Based on Data from Three Large Registries of Congenital Malformations," Pediatr Cardiol, vol. 24(3):195-221, DOI:10.1007/s00246-002-9401-6. (May 2003).
Qiu, et al., Learning Spatio-Temporal Representation with Pseudo-3D Residual Networks, retrieved from the internet URL: https://arxiv.org/abs/1711.10305, 9 pages (2017).
Quartermain M.D., et al., "Variation in Prenatal Diagnosis of Congenital Heart Disease in Infants," Pediatrics, vol. 136(2):e378-e385, doi:10.1542/peds.2014-3783 (Aug. 2015).

(56) References Cited

OTHER PUBLICATIONS

Ruder, et al., Artistic Style Transfer for Videos and Spherical Images, International Journal of Computer Vision, 19 pages (2018).

Salomon L.J., et al., "Practice guidelines for performance of the routine mid-trimester fetal ultrasound scan," Ultrasound Obstet Gynecol, vol. 37(1):116-126, DOI:10.1002/uog.8831. (Jan. 2011).

Schneider C., et al., "Development of Z-scores for fetal cardiac dimensions from echocardiography," Ultrasound Obstet Gynecol, vol. 26(6):599-605, DOI:10.1002/uog.2597. (Nov. 2005).

Simonyan, Two-Stream Convolutional Network for Action Recognition in Videos, Visual Geometry Group, University of Oxford, 9 pages (2014).

Simonyan, Very Deep Convolutional Networks for Large-Scale Image Recognition, Visual Geometry Group, University of Oxford, 14 pages (2015).

Sonio Detect, FDA 510(k), K230365, Jul. 25, 2023, available at https://www.accessdata.fda.gov/cdrh_docs/pdf23/K230365.pdf.

Sonio Detect, User Manual, Nov. 2022, available at: https://sonio.ai/old/pt-br/sonioapp/dt-user-manual-pt-br/.

Stümpflen, Effect of detailed fetal echocardiography as part of routine prenatal ultrasonographic screening on detection of congenital heart disease, The Lancet, 348(9031):854-857 (Sep. 1996).

Suard C., et al., "Accuracy of prenatal screening for congenital heart disease in population: A retrospective study in Southern France," Plos One, vol. 15(10):e0239476, 13 pages, DOI:10.1371/journal.pone.0239476. (Oct. 5, 2020).

Sun, et al., Human Action Recognition using Factorized Spatio-Temporal Convolutional Networks, retrieved from the internet URL: https://arxiv.org/abs/1510.00562, 9 pages (2015).

Sun H.Y., "Prenatal Diagnosis of Congenital Heart Defects: Echocardiography," Translational Pediatrics, vol. 10 (8):2210-2224, doi: 10.21037/tp-20-164. (Aug. 2021).

Szegedy, et al., Going Deeper with Convolutions, 2015 IEEE Conference on Computer Vision and Pattern Recognition (CVPR), 9 pages (Jun. 2015).

Szegedy, Going Deeper with Convolutions, IEEE Conference on Computer Vision and Pattern Recognition (CVPR), 12 pages (2014).

Tran, et al., A Closer Look at Spatiotemporal Convolutions for Action Recognition, retrieved from the internet URL: https://arxiv.org/abs/1711.11248, 10 pages (2018).

Tran, et al., Learning Spatiotemporal Features with 3D Convolutional Networks, IEEE International Conference on Computer Vision (ICCV), 16 pages (2015).

Tune Gaussian Mixture Models, retrieved from the internet URL: https://www.mathworks.com/help/stats/tune-gaussian-mixture-models.html, retrieved on Apr. 13, 2023, 7 pages.

Tworetzky W., et al., "Improved Surgical Outcome After Fetal Diagnosis of Hypoplastic Left Heart Syndrome," Circulation, vol. 103(9):1269-1273, DOI:10.1161/01.CIR.103.9.1269. (Mar. 6, 2001).

Ultrasound in Pregnancy. Practice Bulletin No. 175. American College of Obstetricians and Gynecologists, Obstetrics Gynecology, 128 (6):1459-1460) (Dec. 2016).

Van Nisselrooij A.E.L., "Why Are Congenital Heart Defects Being Missed?" Ultrasound in Obstetrics Gynecology, vol. 55(6):747-757, doi:10.1002/uog.20358 (Jun. 2020).

Varol, et al., Long-term Temporal Convolutions for Action Recognition, retrieved from the internet URL: https://arxiv.org/abs/1604.04494, 8 pages (2017).

Vivaaindrean, Detection of Robbery-Related Concepts Using Deep Learning, Final Year Project, UTAR, 56 pages (Jan. 2020).

Wang, et al., Actions ~ Transformations, retrieved from the internet URL: https://arxiv.org/abs/1512.00795, 10 pages (2016).

Wang, et al., Towards Good Practices for Very Deep Two-Stream ConvNets, retrieved from the internet URL: https://arxiv.org/abs/1507.02159, 5 pages (2015).

"WHO Recommendations on Antenatal Care for a Positive Pregnancy Experience," World Health Organization; 2016, Retrieved from internet URL:https://www.ncbi.nlm.nih.gov/books/NBK409108/ (Dec. 2022).

Wolfe, Deep Learning on Video (Part One): The Early Days, retrieved from the internet URL: https://towardsdatascience.com/deep-learning-on-video-part-one-the-early-days-8a3632ed47d4, 13 pages (2021).

Xie, et al., Rethinking Spatiotemporal Feature Learning: Speed-Accuracy Trade-offs in Video Classification, retrieved from the internet URL: https://arxiv.org/abs/1712.04851, 17 pages (2018).

Carvalho, et al., ISUOG Practice Guidelines (updated): sonographic screening examination of the fetal heart, Ultrasound Obstet. Gynecol., 41:348-359 (2013).

Arnaout, et al., An ensemble of neural networks provides expert-level prenatal detection of complex congenital heart disease, Nature Medicine, 27(5):882-91 (May 2021).

Feng, et al., Two-Stream Attention Spatio-Temporal Network for Classification of Echocardiography Videos, 2021 IEEE 18th International Symposium on Biomedical Imaging (ISBI), pp. 1461-1465 (Apr. 2021).

Fiorentino, et al., A Review on Deep-Learning Algorithms for Fetal Ultrasound-Image Analysis, Medical Image Analysis, 1:83 102629 (Jan. 2023).

Gao, et al., A fused deep learning architecture for viewpoint classification of echocardiography, 36:103-13 (Jul. 2017).

Gao, et al., Detection and Characterization of the Fetal Heartbeat in Free-hand Ultrasound Sweeps with Weakly-Supervised Two-Streams Convolutional Networks, *Medical Image Computing and Computer-Assisted Intervention-MICCAI 2017, 20th International Conference Proceedings, Part II* 20, pp. 305-313, (Sep. 2017).

International Search Report & Written Opinion dated Apr. 29, 2024 in Int'l PCT Patent Appl. Serial No. PCT/IB2024-051622 (0110).

International Search Report & Written Opinion dated May 29, 2024 in Int'l PCT Patent Appl. Serial No. PCT/IB2024-051624 (0210).

Patra, et al., Multi-anatomy localization in fetal echocardiography videos, 2019 IEEE 16th International Symposium on Biomedical Imaging (ISBI 2019), pp. 1761-1764 (Apr. 2019).

Thomas, et al., Light-weight Spatio-Temporal Graphs for Segmentation and Ejection Fraction Prediction in Cardiac Ultrasound, International Conference on Medical Image Computing and Computer-Assisted Intervention, pp. 380-390 (Sep. 2022).

* cited by examiner

SYSTEMS AND METHODS FOR DETECTING CARDIOVASCULAR ANOMALIES USING SPATIOTEMPORAL NEURAL NETWORKS

CROSS-REFERENCE TO RELATED APPLICATIONS

This application is a continuation-in-part of U.S. patent application Ser. No. 18/183,942, filed Mar. 14, 2023, now U.S. Pat. No. 11,875,507, which claims priority to EP patent application Ser. No. 23/305,236.4, filed Feb. 22, 2023, the entire contents of which are incorporated herein by reference.

TECHNICAL FIELD

The present invention relates, in general, to an image processing system, for example, an image processing system with artificial intelligence and machine learning functionality for detecting cardiovascular anomalies.

BACKGROUND

With today's imaging technology, medical providers may see into a patient's body and may even detect abnormalities and conditions without the need for a surgical procedure. Imaging technology such as ultrasound imaging, for example, permits a medical technician to obtain two-dimensional views of a patient's anatomy, such as a patient's heart chambers. For example, echocardiogram uses high frequency sound waves to generate pictures of a patient's heart. Various views may be obtained by manipulating the orientation of the ultrasound sensor with respect to the patient.

Medical imaging may be used by a healthcare provider to perform a medical examination of a patient's anatomy without the need for surgery. For example, a healthcare provider may examine the images generated for visible deviations from normal anatomy. Additionally, a healthcare provider may take measurements using the medical images and may compare the measurements to known normal ranges to identify anomalies.

In one example, a healthcare provider may use echocardiography to identify a heart defect such as ventricular septal defect, which is an abnormal connection between the lower chambers of the heart (i.e., the ventricles). The healthcare provider may visually identify the connection in the medical images and based on the medical images may make a diagnosis. This diagnosis may then lead to surgical intervention or other treatment.

While healthcare providers frequently detect anomalies such as heart defects via medical imaging, defects and various other abnormalities go undetected due to human error, insufficient training, minor visual cues, and various other reasons. This is particularly true with respect to complex anatomy and prenatal imaging. For example, congenital heart defects (CHD) in fetuses are particularly difficult to detect. CHDs during pregnancy are estimated to occur in about one percent of pregnancies. However, between fifty to seventy percent of CHD cases are not properly detected by practitioners. Detection of CHD during pregnancy permits healthcare providers to make a diagnosis and/or promptly provide interventional treatment which could lead to improved fetus and infant health and fewer infant fatalities.

Accordingly, there is a need for improved methods and systems for analyzing and/or processing medical imaging including ultrasound imaging for detecting anomalies and defects such as CHD.

SUMMARY OF THE INVENTION

Provided herein are systems and methods for analyzing medical imaging using spatiotemporal neural networks for detecting cardiovascular anomalies and/or conditions such as CHD. The systems and methods may include processing medical device imaging, such as single frame images and/or video clips generated by an ultrasound system using spatiotemporal convolutional neural networks (CNNs). Optical flow data may be generated based on the image and/or video clips and may indicate movement of pixels in the images and/or video clips. The image and/or video clips may be processed by a spatial CNN and the optical flow data may be processed using a temporal CNN. The spatial output from the spatial CNN and the temporal output from the temporal CNN may be fused to generate a combined spatiotemporal output, which may indicate a likelihood of a presence of one or more CHDs or other cardiovascular anomalies in the patient (e.g., a fetus of a pregnant patient).

A method is provided herein for determining a presence of one or more CHDs and/or other cardiovascular anomalies in a patient. The method may include determining, by a server, first image data representative of a portion of the patient's cardiovascular system, the first image data including a series of image frames, determining optical flow data based on the first image data, the optical flow data indicative of movement of pixels in the series of image frames, processing the image data using a spatial model, the spatial model including one or more first convolutional neural networks trained to process image data, processing the optical flow data using a temporal model, the temporal model including one or more second convolutional neural networks trained to process optical flow data, generating a spatial output using the spatial model and based on the image data, the spatial output indicative of a first likelihood of a presence one or more CHD and/or other cardiovascular anomalies of the patient, generating a temporal output using the temporal model and based on the plurality of optical flow data, the temporal output indicative of a second likelihood of the presence one or more CHD and/or other cardiovascular anomalies of the patient, determining a fused output based on the spatial output and the temporal output, the fused output indicative of a third likelihood of the presence of one or more CHD and/or other cardiovascular anomalies of the patient, causing a first device to display a user interface corresponding to the fused output.

The third likelihood of the presence of one or more CHD and/or other cardiovascular anomalies of the patient may include one or more of a likelihood of a presence of atrial septal defect, atrioventricular septal defect, coarctation of the aorta, double-outlet right ventricle, d-transposition of the great arteries, Ebstein anomaly, hypoplastic left heart syndrome, interrupted aortic arch, ventricular disproportion, abnormal heart size, ventricular septal defect, abnormal atrioventricular junction, abnormal area behind the left atrium, abnormal left ventricle junction, abnormal aorta junction, abnormal right ventricle junction, abnormal pulmonary artery junction, arterial size discrepancy, right aortic arch abnormality, abnormal size of pulmonary artery, abnormal size of transverse aortic arch, or abnormal size of superior vena cava. The method may further include comparing the fused output to a threshold value, determining the fused output satisfies the threshold value, and determining the risk of or presence of the one or more CHD and/or other cardiovascular anomalies of the patient based on the fused output satisfying the threshold value. The method may further include determining a request from a first device to generate a report corresponding to the fused output and causing the first device to generate the report corresponding to the fused output. The method may further include training the spatial model and the temporal model using a plurality of second image data different from the first image data. The method may further include removing at least a portion of the first image data from each of the image frames in the series of image frames.

The method may further include receiving the first image data from an imaging system and the imaging system may include an ultrasound or echocardiogram device. The image data may include a first series of image frames corresponding to a first orientation of the ultrasound device or echocardiogram device and a second series of image frames corresponding to a second orientation of the ultrasound device or echocardiogram device. It is understood that multiple series of image frames may be processed using the imaging system. The method may include sampling the image data such that only non-adjacent image frames in the series of image frames are processed by the spatial model. Image data from adjacent and other image series and/or image frames may be used to process and/or generate an output with respect to a certain image series or image frame. Such other image series and/or image frames may provide context to the image series and/or frame for which an output is generated. One or more of the spatial output may further indicate one or more of key-point data or contour data. One or more of the temporal output may further indicate one or more of key-point data or contour data. The method may further include determining one or more of key-point data or contour data based on the spatial output and the temporal output and/or causing the first device to further display the one or more of key-point data or contour data.

A system is provided herein for determining a presence of one or more CHDs and/or other cardiovascular anomalies in a patient. The system may include memory designed to store computer-executable instructions, and at least one computer processor designed to access memory and execute the computer-executable instructions to determine first image data representative of a portion of the patient's cardiovascular system, the first image data including a series of image frames, determine optical flow data based on the image data, the optical flow data indicative of movement of pixels in the series of image frames, generate a spatial output by processing the image data using a spatial model, the spatial model including one or more first convolutional neural networks and the spatial output indicative of a first likelihood of a presence one or more CHD and/or other cardiovascular anomalies of the patient, generate a temporal output by processing the optical flow data using a temporal model, the temporal model including one or more second convolutional neural networks and the temporal output indicative of a second likelihood of the presence one or more CHD and/or other cardiovascular anomalies of the patient, determine a fused output based on the spatial output and the temporal output, the fused output indicative of a third likelihood of the presence of one or more CHD and/or other cardiovascular anomalies of the patient, and causing a first device to display a user interface corresponding to the fused output.

The third likelihood of the presence of one or more CHD and/or other cardiovascular anomalies of the patient may include one or more of a likelihood of a presence of atrial septal defect, atrioventricular septal defect, coarctation of the aorta, double-outlet right ventricle, d-transposition of the great arteries, Ebstein anomaly, hypoplastic left heart syndrome, or interrupted aortic arch. The computer processor may be further designed to execute the computer-executable instructions to compare the fused output to a threshold value, determine the fused output satisfies the threshold value, and determine the presence of the one or more CHD and/or other cardiovascular anomalies of the patient based on the fused output satisfying the threshold value. The computer processor may be further designed to execute the computer-executable instructions to determine a request from a first device to generate a report corresponding to the fused output, and cause the first device to generate the report corresponding to the fused output. The computer processor may be further designed to execute the computer-executable instructions to train the spatial model and the temporal model using a plurality of second image data different from the first image data. The computer processor may be further designed to execute the computer-executable instructions to remove at least a portion of the first image data from each of the image frames in the series of image frames.

The computer processor may be further designed to execute the computer-executable instructions to receive the first image data from an imaging system and the imaging system may include an ultrasound or echocardiogram device. The image data may include a first series of image frames corresponding to a first orientation of the ultrasound device or echocardiogram device and a second series of image frames corresponding to a second orientation of the ultrasound device or echocardiogram device. The computer processor may be further designed to execute the computer-executable instructions to sample the image data such that only non-adjacent image frames in the series of image frames are processed by the spatial model. One or more of the spatial output may further indicate one or more of key-point data or contour data. One or more of the temporal output may further indicate one or more of key-point data or contour data. The system may further be designed to execute the computer-executable instructions to determine one or more of key-point data or contour data based on the spatial output and the temporal output and/or cause the first device to further display the one or more of key-point data or contour data.

The foregoing summary is illustrative only and is not intended to be in any way limiting. In addition to the illustrative aspects, embodiments, and features described above, further aspects, embodiments, and features will become apparent by reference to the following drawings and the detailed description.

Figure 1:
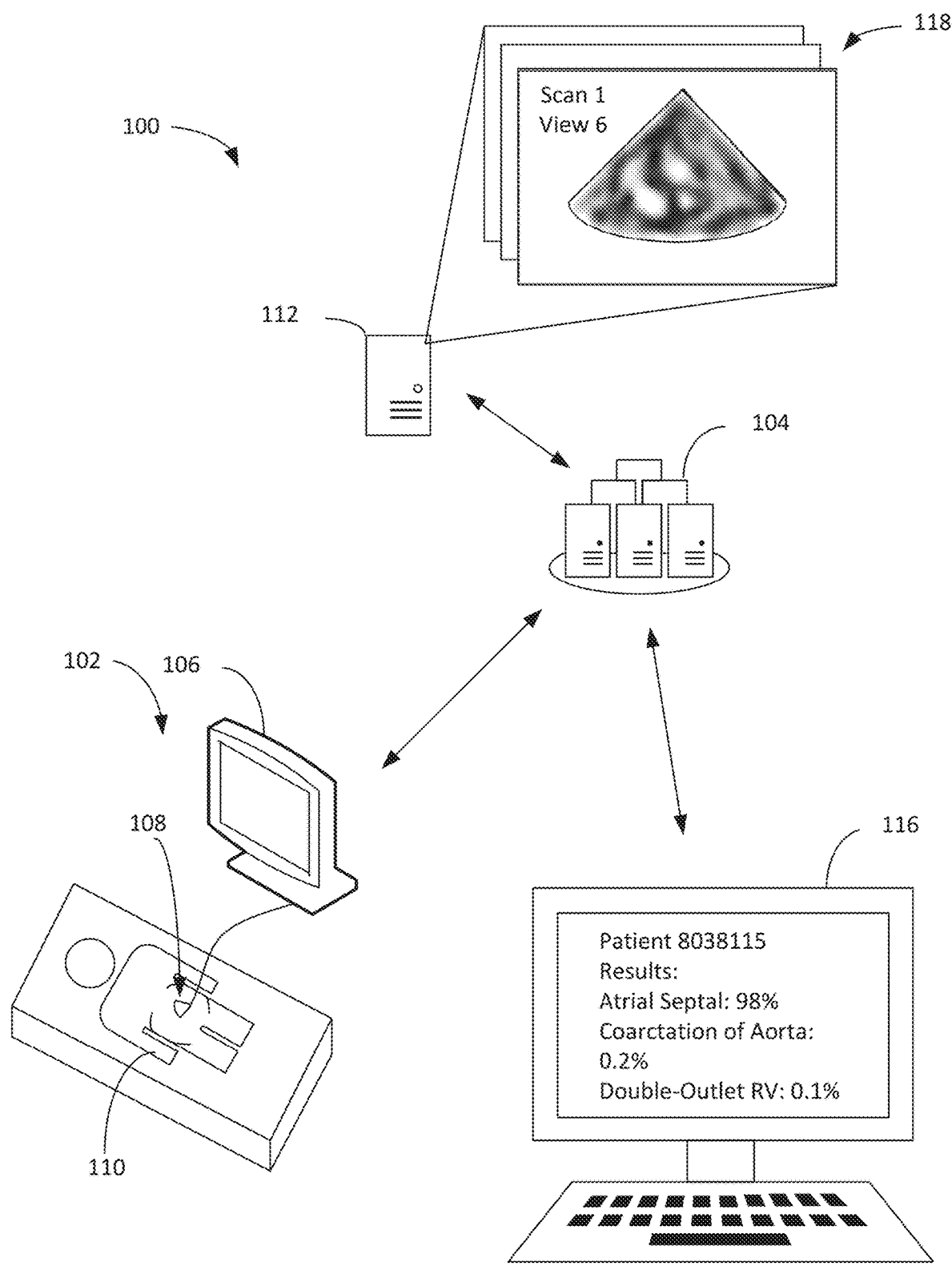
FIG. 1 illustrates an image processing system for determining the presence of a cardiovascular anomaly, in accordance with some aspects of the present invention.

The foregoing and other features of the present invention will become apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

DETAILED DESCRIPTION OF THE INVENTION

The present invention is directed to an image processing system using artificial intelligence and machine learning to determine a likelihood of a presence or absence of a CHD and/or other cardiovascular anomalies in a patient, such as a fetus during pregnancy, or that such presence or absence is inconclusive. For example, medical imaging such as images (e.g., still frames and/or video clips) may be generated using an ultrasound system (e.g., an echocardiogram system) and may be processed by spatiotemporal neural networks for generating a likelihood of a presence or absence of one or more CHD and/or other cardiovascular anomaly. The images may also be processed by the spatiotemporal neural network to determine detection of key-points corresponding to cardiovascular anatomy (e.g., the apex of the heart, etc.), such data referred to as key-point data, and/or contours and/or segmentation of elements and/or features of the cardiovascular anatomy (e.g., the contours of one or more ventricles, one or more atria, etc.), such data referred to as contour data, and this information may be used to compute measurements (e.g., length, area, ratios) and/or be used for the detection of features and/or anatomy of the fetus (e.g., detection of the heart, the lung, parts of the heart such as the atria, the septum, the ventricles, and the like).

The medical imaging may include a consecutive series of still frame images. The still frame images may be pre-processed to remove excess or unwanted portions. For example, during preprocessing, spatial, temporal, and/or spatiotemporal filters may be used to remove noise. The still frame images may be sampled, segmented, or parsed such that only a certain number of frames may be selected (e.g., every second, third, fourth frame). Optical flow data may be generated from the image data and may represent movement of pixels in the image data. The optical flow data and the image data (e.g., single frames of image data) may be processed in parallel using two neural networks, one on the image and the other on the optical flow data. The architecture of these two networks may be fused at one or more levels (e.g., late fusion and/or the last feature map).

The two parallel neural networks may be two CNNs. Specifically, a first CNN may be a spatial network trained to process image data (e.g., single frames of RGB data). The second CNN may be a temporal neural network trained to process optical flow data. Alternatively, or additionally, one or more neural network may be a deep neural network (DNN) and/or any other suitable neural network. Each neural network may output a likelihood of a presence, absence, and/or inconclusiveness of CHD and/or other cardiovascular anomaly and/or the output may be indicative of key-points and/or contours of anatomy of the fetus. The architecture of the two neural networks may be fused to generate a superior result as compared to either network individually. For example, outputs may be determined using both networks and merged via late fusion to make a single spatiotemporal output that indicates the likelihood of a presence, absence, and/or inconclusiveness of CHD and/or other anomaly in the image data (e.g., based on the visual appearance of the anatomy or the lack of or absence or certain anatomy). It is understood that one or more CNN may optionally be an attention-based neural network. It is further understood that the spatial network and the temporal network may be a single network or may be two networks. For example, the imaging system may include a dual stream network having a two-stream architecture with a spatial CNN and a temporal CNN and may fuse the CNNs. While the imaging processing systems described herein are described as CNNs, it is understood that such imaging processing systems are not limited to CNNs and other embodiments of the imaging processing systems may alternatively use any combination of neural networks such as one or more of CNNs, residual neural networks, attention neural networks, region-based convolutional neural networks (RCNN), and/or any other suitable neural network.

Referring now to FIG. 1, image processing system 100 is illustrated. Image processing system 100 may be designed to receive medical images, process medical images using artificial intelligence and machine learning, and determine a likelihood of a presence, absence, or inconclusiveness of one or more CHD and/or other cardiovascular anomaly and/or image processing system 100 may be used to determine an output indicative of key-points and/or contours of anatomy of the fetus. For example, image processing system 100 may receive image data showing anatomy of a fetus and may process the image data using spatiotemporal CNNs to automatically determine the presence and/or absence of one or more CHD and/or other cardiovascular anomaly.

Image processing system 100 may include one or more imaging system 102 that may each be in communication with a server 104. For example, imaging system 102 may be any well-known medical imaging system that generates image data (e.g., still frames and/or video clips including RGB pixel information) such as an ultrasound system, echocardiogram system, x-ray systems, computed tomography (CT) systems, magnetic resonance imaging (MRI) systems, positron-emission tomography (PET) systems, and the like.

Imaging system 102 may be any suitable ultrasound scan system for performing fetal ultrasound examinations (e.g., second-trimester fetal anatomic ultrasound examinations between 18 and 24 weeks of gestation, first-trimester examinations, third-trimester fetal examinations, fetal echocardiography, or otherwise), however, the inventive software/programming described herein is stored and executed on imaging system 102, server 104, and/or datastore 112. In one example, imaging system may be Samsung's WS80A ultrasound system, or any other suitable ultrasound scan system. Image processing system 100 may optionally be designed to be agnostic to the manufacturer, model, and/or type of imaging system 102. For example, image processing system 100 may implement and/or incorporate systems and/or methods for agnostic analysis provided in U.S. Pat. No. 11,861,838, the entire contents of which are incorporated herein by reference. While ultrasound systems are described throughout, it is understood that the same or a similar approach may be used with any other suitable medical imaging system (e.g., CT system, MRI system, PET system, or any other imaging and/or diagnostic system).

As shown in FIG. 1, imaging system 102 may be an ultrasound imaging system including ultrasound sensor 108 and ultrasound device 106. Ultrasound sensor 108 may include a piezoelectric sensor device and may be any well-known ultrasound sensing device. Ultrasound device 106 may be any well-known computing device including a processor and a display and may have a wired or wireless connection with ultrasound sensor 108.

Ultrasound sensor 108 may be used by a healthcare provider to obtain image data of the anatomy of a patient (e.g., patient 110). Ultrasound sensor 108 may generate two-dimensional images corresponding to the orientation of ultrasound sensor 108 with respect to patient 110. The image data generated by ultrasound sensor 108 may be communicated to ultrasound device 106. Ultrasound device 106 may send the image data to remote server 104 via any well-known wired or wireless system (e.g., Wi-Fi, cellular network, Bluetooth, Bluetooth Low Energy (BLE), near field communication protocol, etc.). Additionally, or alternatively, image data may be received and/or retrieved from one or more picture archiving and communication system (PACS). For example, the PACS system may use a Digital Imaging and Communications in Medicine (DICOM) format. Any results from the system (e.g., spatiotemporal output 232 and/or analyzed output 236) may be shared with PACS.

Remote server 104 may be any computing device with one or more processors capable of performing operations described herein. In the example illustrated in FIG. 1, remote server 104 may be one or more server, desktop or laptop computer, or the like and/or may be located in a different location than imaging system 102. Remote server 104 may run one or more local applications to facilitate communication between imaging system 106, datastore 112, and/or analyst device 116.

Datastore 112 may be one or more drives having memory dedicated to storing digital information such as information unique to a certain patient, professional, facility and/or device. For example, datastore 112 may include, but is not limited to, volatile (e.g. random-access memory (RAM)), non-volatile (e.g. read-only memory (ROM)), flash memory, or any combination thereof. Datastore 112 may be incorporated into server 104 or may be separate and distinct from server 104. In one example, datastore 112 may be a picture archiving and communication system (PACS).

Remote server 104 may communicate with datastore 112 and/or analyst device 116 via any well-known wired or wireless system (e.g., Wi-Fi, cellular network, Bluetooth, Bluetooth Low Energy (BLE), near field communication protocol, etc.). Datastore 112 may receive and store image data (e.g., image data 118) received from remote server 104. For example, imaging system 102 may generate image data (e.g., ultrasound image data) and may send such image data to remote server 104, which may send the image data to datastore 112 for storage. It is understood that datastore 112 may be optional and/or more than one imaging system 102, remote server 104, datastore 112 and/or analyst device 116 may be used.

Analyst device 116 may be any computing device having a processor and a display and capable of communicating with at least remote server 104 and performing operations described herein. Analyst device 116 may be any well-known computing device such as a desktop, laptop, smartphone, tablet, wearable, or the like. Analyst device 116 may run one or more local applications to facilitate communication between analyst device 116 and remote server 104 and/or any other computing devices or servers described herein.

Remote server 104 may receive image data (e.g., RGB image data from an ultrasound system) from datastore 112 and/or image system 106 and may process the image data to determine a presence or absence of CHD and/or any other cardiovascular anomaly in a patient (e.g., in a fetus of a pregnant person) and/or key-points and/or contours of anatomy of the fetus. For example, remote server 104 may process one or more trained models such as CNNs trained to detect one or more CHDs and/or anomalies.

Remote server 104 may use two parallel spatiotemporal convolutional neural networks (CNNs) and may fuse the outputs to generate a superior output having improved accuracy over the individual CNNs. The first CNN may be a spatial CNN and the second may be a temporal CNN. The image data, which may be ultrasound image frames, may be processed by the spatial CNN.

Optical flow data may be generated based on the image and/or video clips and may indicate movement of pixels in the images and/or video clips. The optical flow data may be processed using a temporal CNN. The spatial output from the spatial CNN and the temporal output from the temporal CNN may be fused to generate a combined spatiotemporal output, which may indicate a likelihood of a presence or absence of one or more CHDs and/or other cardiovascular anomaly in the patient (e.g., the fetus of a pregnant patient) and/or key-points and/or contours of anatomy of the fetus. Remote server 104 may cause analyst device 116 to display information about the likelihood of a presence of one or more CHDs and/or other cardiovascular anomalies. For example, analyst device may display a patient ID number and a likelihood percentage for one or more CHDs and/or other cardiovascular anomalies.

In one example, system 100 may be the same as or similar to the systems and methods for computer assisted diagnostic aid for use in fetal ultrasound exams provided in U.S. Pat. No. 11,869,188, issued on Jan. 9, 2024, and U.S. patent application Ser. No. 18/406,446, filed on Jan. 8, 2024, the entire contents of each of which are incorporated herein by reference.

Figure 2A:
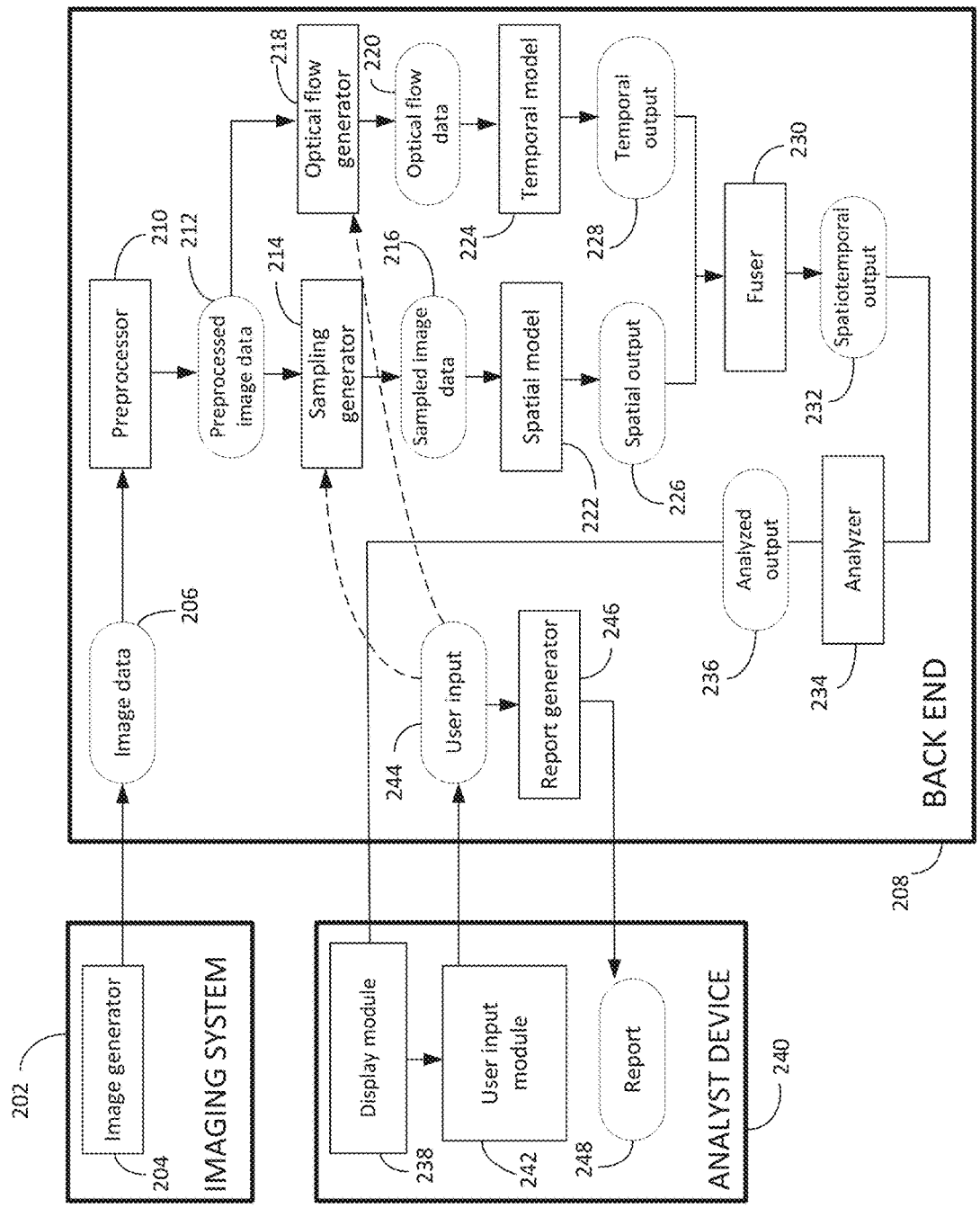
FIGS. 2A-2B illustrates a schematic view of data flow between an imaging system, analyst device, and back end of an image processing system.
Figure 2B:
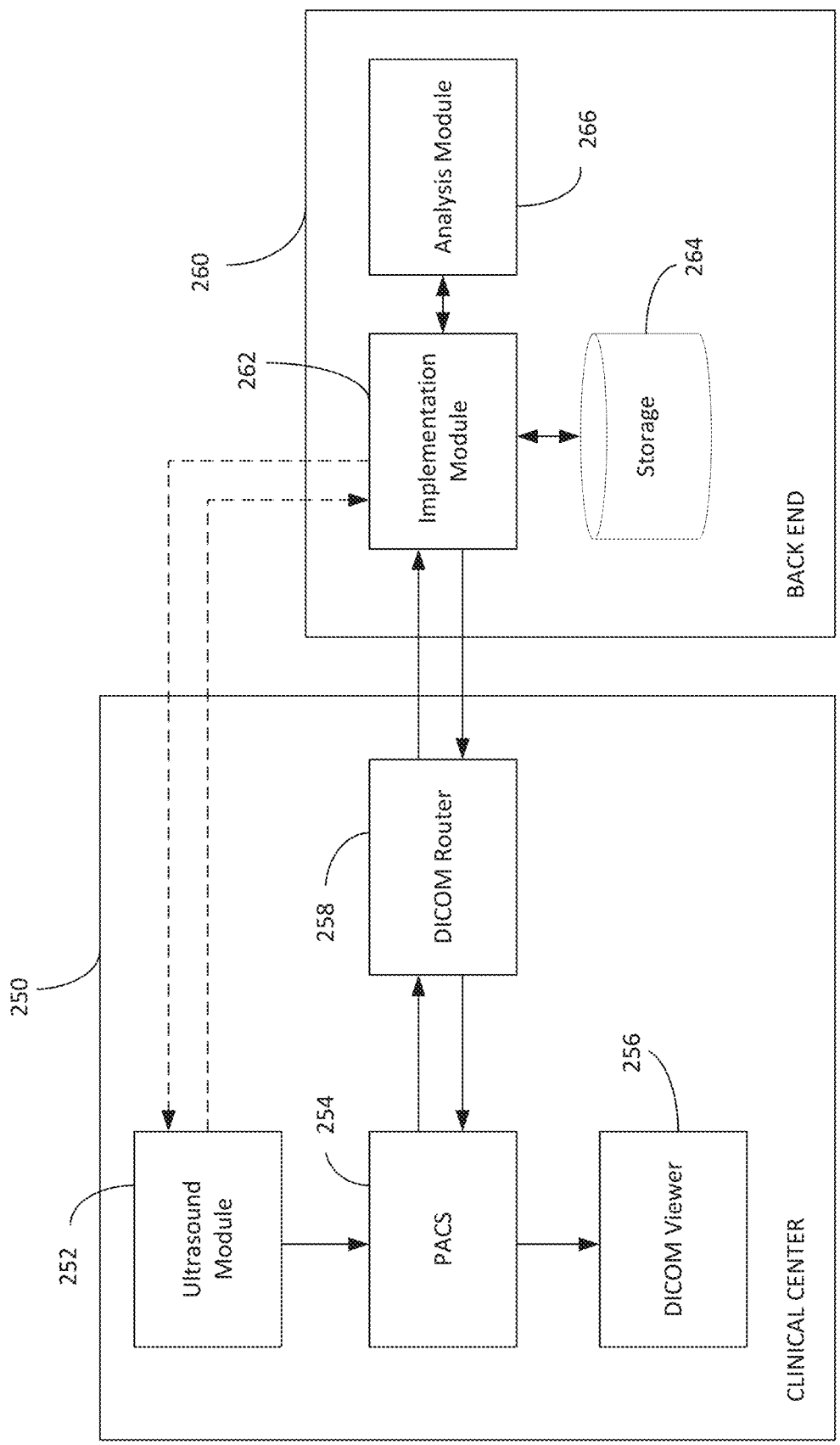

Referring now to FIGS. 2A-2B, schematic views of the data flow between an imaging system, analyst device, and back end of the image processing system are depicted. As shown in FIG. 2A, imaging system 202, which may be the same as or similar to imaging system 102 of FIG. 1, may include image generator 204 which may generate image data 206. Image data 206 may include still frames and/or video clips and may include RGB and/or grey scale pixel information. For example, image data 206 may include two-dimensional representations of ultrasound scans of the patient's anatomy. Additionally, or alternatively, image data 206 may include Doppler image information (e.g., color Doppler, power Doppler, spectral Doppler, Duplex Doppler, and the like). It is understood that various types of image data 206 may be simultaneously processed by imaging system 202. In one example, the Doppler image data may be generated at the same time as ultrasound image data.

Imaging system 202 may send image data 206 to backend 208, which may be the same as or similar to server 104 of FIG. 2A. Image data 206 may be processed by preprocessor 210. Preprocessor 210 may focus, crop, resize and/or otherwise remove unnecessary areas of image data 206 to generate preprocessed image data 212. For example, the black background and text in a still frame generated by imaging system 202 may be removed. Preprocessor may additionally, or alternatively, generate a consecutive series of still frame images from video clips.

Preprocessed image data may optionally be sent to sampling generator 214, which may cause preprocessed image data 212 to be sampled, parsed and/or segmented to generate sampled image data 216. For example, sampling generator 214 may determine intervals (e.g., intervals of two, three, four, etc.) of frames to be sampled. In this manner, only the sampled frames of image data 212 may be processed by neural networks at backend 208. Sampling image data 212 may permit the networks to process image frames over a greater time period of image data 212.

Preprocessed image data 212, image data 206, and/or sampled image 216 data may be processed by optical flow generator 218 to generate optical flow data 220 corresponding to preprocessed image data 212, image data 206, and/or sampled image 216 data. Optical flow data 220 may permit the networks to better consider the movement of the image data over time.

To generate optical flow data 220, consecutive image frames of image data 212, image data 206, and/or sampled image 216 may be input to optical flow generator 218. From the consecutive image frames, horizontal and vertical optical flow data may be computed for each adjacent frames, resulting in an output size of H×W×2 L where H and W are the height and width of the image frames and L is the length (e.g., time between frames). The optical flow generator 218 may thereby encode the motion of individual pixels across frames of the image data 212, image data 206, and/or sampled image 216 to capture movement illustrated in the images across time.

Sampled image data 216, pre-processed image data 212, and/or image data 206 may then be applied to spatial model 222 to generate spatial output 226 which may be a spatial CNN such as an spatial CNN trained for image processing. Spatial model 222 may be trained to analyze image data (e.g., RGB data) to determine in each frame a presence of one or more CHD and/or other cardiovascular anomaly. It is understood that spatial model 222 may optionally take as an input temporal output 228 from temporal model 224.

Spatial output 226 may include a vector or matrix including a score or value for one or more frames corresponding to the likelihood of CHD and/or other cardiovascular anomaly. Spatial output 226 may, optionally, further include a score or value indicative of a likelihood of one or more views or orientations of the sensor device for which the image data corresponds to. For example, various views may include anatomic standard views (e.g., 4 chamber view, left ventricular outflow tract, right ventricular outflow tract, etc.). Such views may have standard orientations with respect to the respective anatomy (e.g., top view, bottom view, left view, right view, above, below, etc.). Each view and likelihood value may be depicted in a vector or matrix. In one example, spatial output 226 may include low likelihood of views for bottom, right, and left, but a high likelihood of a top down view. This would indicate that the view is likely from the top.

Similarly, optical flow data 220 may be applied to temporal model 224, which may be a temporal CNN such as an temporal CNN trained for image processing and/or trained for processing optical flow data to generate temporal output 228. For example, temporal model 224 may generate temporal output 228 which may indicate for each optical flow data set a score or value indicative of a likelihood of a presence of one or more CHD and/or other cardiovascular anomaly. Temporal output 228 may optionally further include a score or value indicative of a likelihood of one or more views or orientations of the sensor device for which the image data corresponds to. It is understood that temporal model 224 may optionally take as an input spatial output 226 from spatial model 222.

Spatial output 226 and temporal output 228 may both be input into fuser 230 to fuse spatial model 222 and temporal model 224 to generate spatiotemporal output 232, which may be similar to spatial output 226 and temporal output 228, but with improved accuracy. For example, fuser 230 may combine architecture of spatial model 222 and temporal model 224 at several levels (e.g., the last feature map). Alternatively, or additionally, a weighted average of spatial output 226 and temporal output 228 may be determined to generate spatiotemporal output 232.

It is understood that various well-known fusion approaches may be used such as sum, max, concatenate, convolutional, and bilinear. It is further understood that while late fusion may be used, other techniques such as early fusion (changing the first convolution layer of each stream to a three-dimensional convolution), or slow fusion (changing all convolutional layers within each stream to be three-dimensional convolutions with a smaller temporal extent in comparison to early fusion) may be used.

Spatiotemporal output 232 may be processed by analyzer 234 which may process spatiotemporal output 232 generate analyzed output 236 which may indicate a presence or absence, or inclusiveness of the presence or absence, of one or more CHD and/or cardiovascular anomalies in image data 206 and/or may indicate key-points and/or contours of anatomy of the fetus. For example, analyzer 234 may calculate weighted averages based on spatiotemporal output 232 and/or may filter certain portions of spatiotemporal output 232. In one example, analyzed output 236 and/or spatiotemporal output 232 may indicate the risk of a likelihood of a presence or absence of one or more morphological abnormalities or defects and/or may indicate the presence or absence of one or more pathologies. For example, analyzed output 236 and/or spatiotemporal output 232 may indicate the presence of, or may be used to determine the presence of or likelihood of the presence of, overriding artery (e.g., artery going out of the left ventricle is positioned over a ventricular septal defect), septal defect at the cardiac crux (e.g., the septal defect located at the crux of the heart, either of the primum atrial septum or of the inlet ventricular septum), parallel great arteries, enlarged cardiothoracic ratio (e.g., ratio of the area of the heart to the thorax measured at the end of diastole above 0.33), right ventricular to left ventricular size discrepancy (e.g., ratio of the areas of the right and left ventricles at the end of diastole above 1.4 or below 0.5), tricuspid valve to mitral valve annular size discrepancy (e.g., ratio between the tricuspid and mitral valves at the end of diastole above 1.5 or below 0.65), pulmonary valve to aortic valve annular size discrepancy (e.g., ratio between the pulmonary and aortic valves at the end of systole above 1.6 or below 0.85), abnormal outflow tracts relationship (e.g., absence of the typical anterior-posterior cross-over pattern of the aorta and pulmonary artery), and cardiac axis deviation (e.g., cardiac axis (angle between the line bisecting the thorax and the interventricular septum) below 25° or above 65°), atrial septal defect, atrioventricular septal defect, coarctation of the aorta, double-outlet right ventricle, d-transposition of the great arteries, Ebstein anomaly, hypoplastic left heart syndrome, interrupted aortic arch, ventricular disproportion (e.g., the left or right ventricle larger than the other), abnormal heart size, ventricular septal defect, abnormal atrioventricular junction, increased or abnormal area behind the left atrium, abnormal left ventricle and/or aorta junction, abnormal right ventricle and/or pulmonary artery junction, great arterial size discrepancy (e.g., aorta larger or smaller than the pulmonary artery), right aortic arch abnormality, abnormal size of pulmonary artery, transverse aortic arch and/or superior vena cava, a visible additional vessel, abnormal ventricular asymmetry, pulmonary and/or aortic valve stenosis, ventricular hypoplasia and/or univentricular heart, and/or any other morphological abnormality, defect and/or pathology. Alternatively, or additionally, analyzed output 236 and/or spatiotemporal output 232 may indicate the presence, or may be used to determine the presence of or likelihood of the presence of, any other morphological abnormalities, conditions, and/or disorders.

Back end 208 may communicate analyzed output 236 and/or information based on the spatiotemporal output 232 to analyst device 240, which may be the same as or similar to analyst device 116. Analyst device 240 may be different than or the same as the device in imaging system 202. Display module 238 may generate a user interface on analyst device 240 to generate and display a representation of analyzed output 244 and/or spatiotemporal output 232. The representation may be the same as or similar to graphic user interfaces described and/or illustrated in U.S. application Ser. No. 18/406,446, filed on Jan. 8, 2024, the entire contents of which are incorporated herein by reference. For example, the display may show a representation of the image data (e.g., ultrasound image) with an overlay indicating the location of the detected risk or likelihood of CHDs and/or other cardiovascular anomalies. In one example the overlay could be a box or any other visual indicator (e.g., arrow).

User input module 242 may receive user input 244 and may communicate user input 244 to back end 208. User input 244 may be instructions from a user to generate a report or other information such as instructions that the results generated by one or more of spatial model 222, temporal model 224, and/or fuser 230 are not accurate. For example, where user input 244 indicates an inaccuracy, user input 244 may be used to further train spatial model 222, temporal model 224, and/or fuser 230.

Where user input 244 indicates a request for a report, user input 244 may be communicated to report generator 246, which may generate a report. For example, the report may include some or all of analyzed output 236, spatiotemporal output 232, user input 244, and/or analysis, graphs, plots, tables regarding the same. Report 248 may then be communicated to analyst device 240 for display (e.g., by display module 238) of report 248, which may also be printed out by analyst device 240.

Referring now to FIG. 2B, a clinical workflow of the system illustrated in FIG. 1 is illustrated. As shown in FIG. 2B, clinical center 250 may communicate with back end 260, which may be running on a server (e.g., server 104 of FIG. 1). Clinical center 250 may include ultrasound module 252 which may run on an imaging system (e.g., imaging system 102 of FIG. 1), as well as Picture Archiving and Communication (PACS) system 254, Digital Imaging and Communications in Medicine (DICOM) viewer 256, and DICOM router 258.

Ultrasound module 252 may generate, receive, obtain, and/or store ultrasound images (e.g., image data such as motion video clips and image frames). The image data may be communicated from ultrasound module 252 to PACS system 254 and/or directly to implantation module 262 of backend 260. PACS system 254 may securely store image data received from ultrasound module 252. The image data saved in PACS system 254 may electronically label the record based on user selection input. Once the image data is saved and/or labeled in PACS system 254, DICOM router 258 may connect to PACS system 254 to retrieve the image data and may also connect to back-end 260, which may run on a server (e.g., server 104 and/or datastore 112 of FIG. 1). For example, DICOM router 258 may be connected to implementation module 262 and may send the image data to implementation module 262.

In one example, DICOM router 258 may pseudonymize files so that only pseudonymized files are sent to the back end 260. For example, all patient information may be removed except for certain necessary variables (e.g. fetal age), and pseudonym identifiers may be added to the file for the exam and/or for each recording. Once DICOM router 258 receives outputs from back end 260, it may then perform re-identification, by replacing the pseudonym identifiers with the patient information. Implementation module 262 may upload the image data to storage 264. For example, storage 264 may store encrypted and otherwise secured image data.

Implementation module 262 may retrieve certain image data from storage 264 and may communicate such image data to analysis module 266. Analysis module 266 may process the image data using machine learning algorithms to identify the presence, absence, or inconclusiveness of the presence or absence of one or more CHD and/or cardiovascular anomalies in the image data and/or may indicate key-points and/or contours of anatomy of the fetus. For example, analysis module 266 may run one or more modules or models described with respect to back end 260 of FIG. 2A. For example, analysis module 266 may run spatial model 222, temporal model 224, and/or fuser 230.

The outcomes and/or outputs of analysis module 266 may be stored in storage 264. The outcomes and/or outputs (e.g., spatiotemporal output 232 and/or analyzed output 236 of FIG. 2A) as well as any reports (e.g., report 248), may be communicated back to DICOM router 258 and stored in PACS 254. Once stored in PACS 254, a healthcare provider (e.g., physician) using DICOM viewer 256 may access the outcomes and/or outputs from PACS 254 and view the outcomes and/or outputs (e.g., using a healthcare provider device).

Figure 3A:
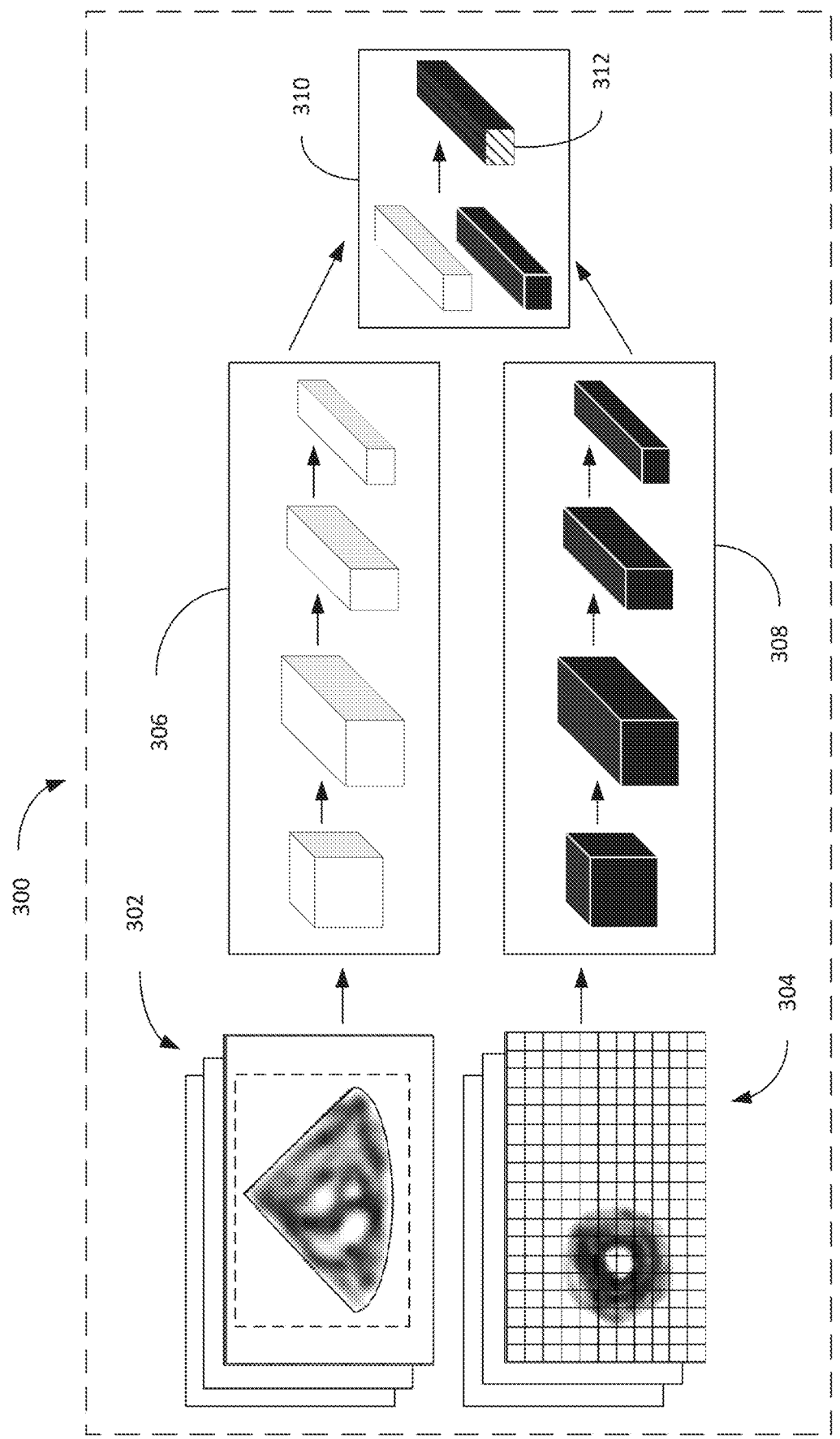
FIGS. 3A-3C illustrate a schematic view of a spatial stream, temporal stream, and fused spatiotemporal output.
Figure 3B:
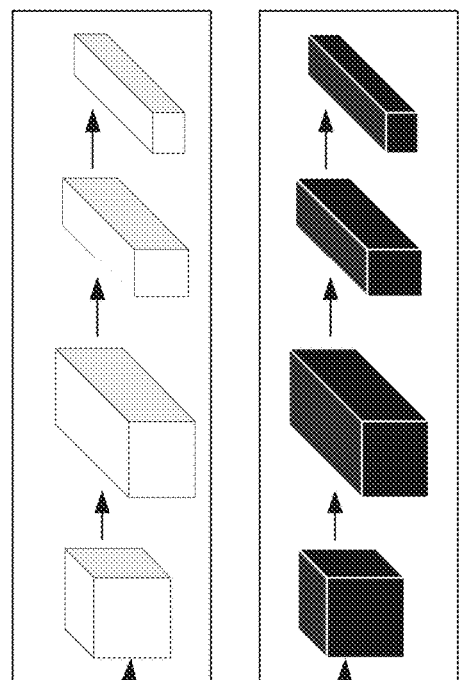
Figure 3C:
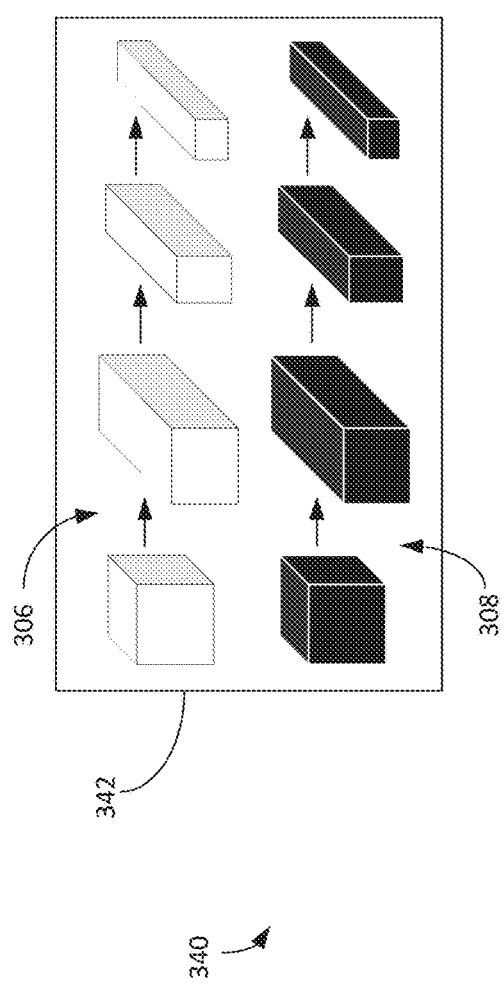

Referring now to FIGS. 3A-3C, spatiotemporal neural networks (e.g., CNNs) are illustrated. Referring now to FIG. 3A, spatiotemporal CNN system 300 is illustrated. Spatiotemporal CNN system 300 may be either a single CNN that may have a two stream architecture or may be independent CNNs. Spatiotemporal CNN system 300 may be the same as or similar to the CNN system used by back end 208 of FIG. 2A. As shown in FIG. 3A, spatiotemporal CNN system 300 may include spatial stream 306 and temporal stream 308, which may be parallel streams that may be combined at fusion 310.

As shown in FIG. 3A, image data 302 may be input into and processed by spatial stream 306 and optical flow data 304 may be input into and processed by temporal stream 308. Spatial stream 306 and temporal stream 308 may be different CNNs or may be streams in the same CNN. Image data 302 may be the same as or similar to image data 206, preprocessed image data 212, and/or sampled image data 216 of FIG. 2A. Optical flow data 220 may be the same as or similar to optical flow data 220 of FIG. 2A.

Spatial stream 306 may receive a single image frame of image data 302 and temporal stream 306 may receive a fixed-sized group of optical flow data 304. For example, the single frame of image data 302 may include RGB pixel information and/or the fixed-sized group of optical flow data 304 may include a fixed-size map and/or plot of optical flow data 304. Spatial stream 306 may simultaneously process image data 302 as temporal stream 306 processes optical flow data 304. The optical flow data processed by the temporal stream 308 may correspond to or may be based on the image data processed by the spatial stream.

Where CNN system 300 includes multiple CNNs, Spatial stream 306 may include one or more spatial CNNs such as an spatial CNN trained for image processing. The spatial CNN may include one or more neural networks (e.g., CNNs) trained to analyze image data (e.g., RGB pixel data) generally (e.g., not specific to medical imaging) and/or one or more neural networks trained to analyze image data in medical imaging (e.g., ultrasound images). For example, the spatial CNN may be trained to analyze ultrasound image data (e.g., RGB pixel data) to determine in each frame a likelihood of a presence or absence of one or more CHD and/or other cardiovascular anomaly and/or a likelihood of a certain view of orientation corresponding to the image data.

Temporal stream 308 may include one or more temporal CNNs such as a temporal CNN trained for image processing and/or trained for processing optical flow data to generate a temporal output. For example, the temporal CNN may generate a temporal output which may indicate for each optical flow data set a presence of one or more CHD and/or other cardiovascular anomaly and/or a likelihood of a certain view or orientation corresponding to the optical flow data.

Fusion 310 may combine the architecture and/or output of the architecture of spatial stream 306 and temporal stream 308, resulting in spatiotemporal output 312. Spatial stream 306 and temporal stream 308 may be fused at one or more levels. As shown in FIG. 3, late fusion may be used such that the outputs from both CNNs and/or both streams are merged to make a single spatiotemporal representation that indicates a likelihood of a presence or absence, or inconclusiveness of the such a presence or absence, of one or more CHD and/or other cardiovascular anomaly, a likelihood of a certain view or orientation corresponding to the image data, and/or may indicate key-points and/or contours of anatomy of the fetus.

It is understood that the two-dimensional CNN illustrated in FIG. 3A may be extended to take as an input not a single image but instead multiple images (e.g., multiple frames) by stacking the filters in the temporal dimension and dividing the weights. For example, filters may be stacked K times in the temporal dimension for K image frames and the weights may be divided by K. While the two streams in FIG. 3A are illustrated as parallel streams, alternatively, temporal stream 308 may take the output of spatial stream 306 as an input to temporal stream 308. It is further understood that other representations may be determined and/or processed along with the spatial and temporal representations.

Referring now to FIGS. 3B-3C, spatiotemporal neural networks are provided with a fusion neural network. For example, neural network systems (e.g., CNN systems 330 and 340) may include Fusion CNN 336 and 344, respectively, which may be similar to fusion 310 of FIG. 3A, but may be a separate neural network. For example, fusion CNN 336 and/or fusion 334 may be a CNN that is trained to output such a spatiotemporal representation based on outputs from spatial stream and temporal stream 308.

As shown in FIG. 3B, spatial stream 306 may be CNN 332 which may be one or more spatial CNNs trained for image processing and/or trained to analyze image data (e.g., RGB pixel data) to determine in each frame a likelihood of a presence of one or more CHD and/or other cardiovascular anomaly and/or a likelihood of a certain view of orientation corresponding to the image data, a likelihood of a certain view or orientation corresponding to the image data, and/or indicate key-points and/or contours of anatomy of the fetus. Similarly, temporal stream 308 may be CNN 334 which may be one or more temporal CNNs such as a temporal CNN trained for image processing and/or trained for processing optical flow data to generate a temporal output. The output of spatial stream 306 and temporal stream 308 may be input into fusion CNN 336 which may be one or more CNNs, which may be trained to output a spatiotemporal representation of spatial output and temporal output. As shown in FIG. 3B, each of spatial stream 306 and temporal stream 308 may be standalone CNNs and together with fusion CNN 336 may total three or more neural networks (e.g., three or more CNNs).

As shown in FIG. 3C, spatial stream 306 and temporal stream 308 may be included in CNN 342 which may be one or more CNNs having steams trained to analyze image data (e.g., RGB pixel data) to determine in each frame a likelihood of a presence of one or more CHD and/or other cardiovascular anomaly, a likelihood of a certain view of orientation corresponding to the image data, and/or indicate key-points and/or contours of anatomy of the fetus. The output of spatial stream 306 and temporal stream 308 may be input into fusion CNN 344 which may be one or more CNNs, which may be trained to output a spatiotemporal representation of spatial stream and temporal stream. As shown in FIG. 3C, each of spatial stream 306 and temporal stream 308 may be included in CNN 342, which together with fusion CNN 336 may total two or more neural networks (e.g., two or more CNNs).

Figure 4:
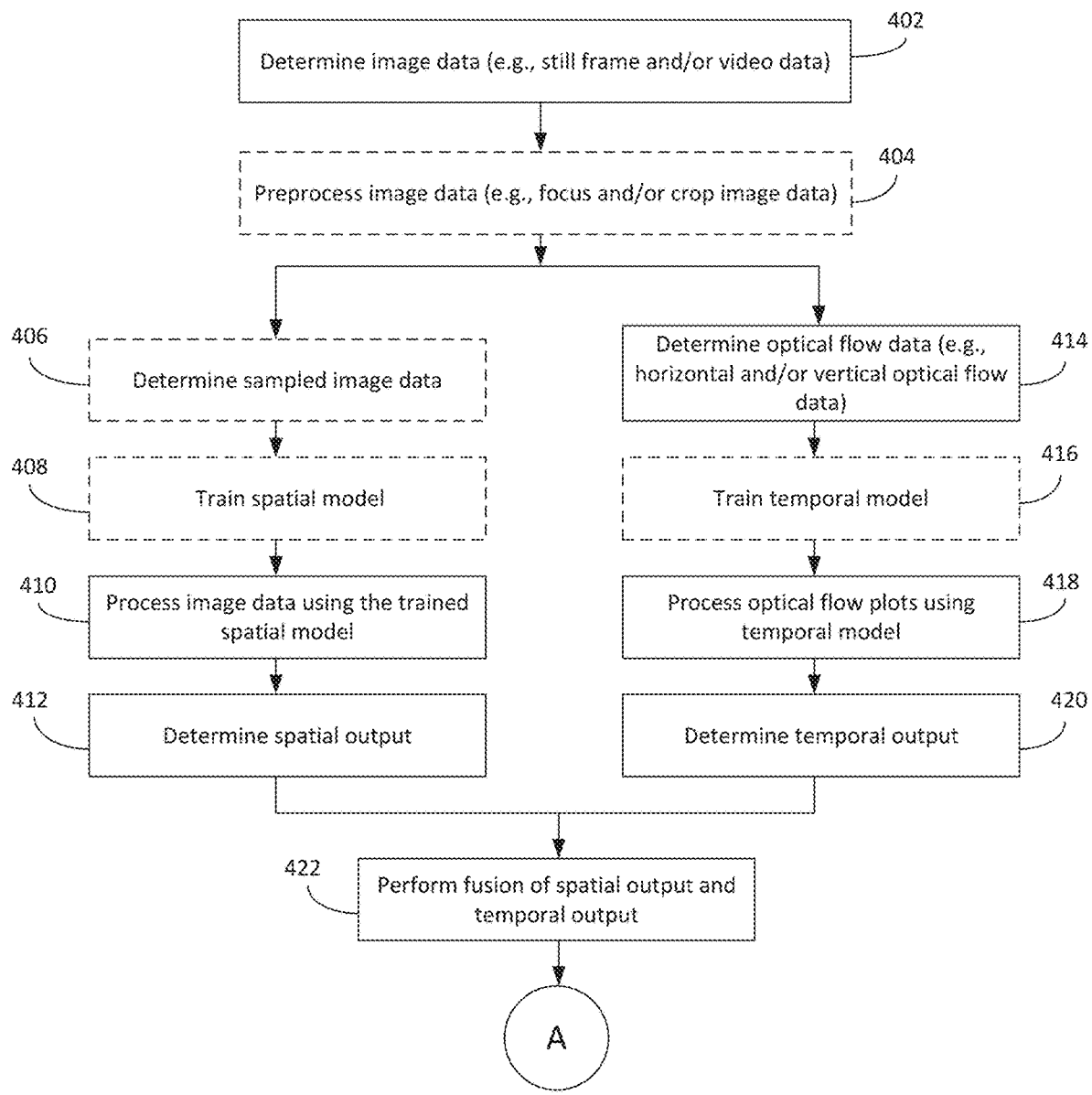
FIG. 4 illustrates a process flow for the spatial CNN, temporal CNN, and fused spatiotemporal output.

Referring now to FIG. 4, a process flow is depicted for generating a spatiotemporal output indicating a likelihood of CHD and/or other cardiovascular anomaly and/or indicating a likelihood of a certain view of orientation of the imaging device (e.g., ultrasound sensor). Some or all of the blocks of the process flows in this disclosure may be performed in a distributed manner across any number of devices (e.g., a server such as server 104 of FIG. 1, computing devices, imaging or sensor devices, or the like). Some or all of the operations of the process flow may be optional and may be performed in a different order.

At block 402, computer-executable instructions stored on a memory of a device, such as a server, may be executed to determine image data. For example, the image data may be the same as or similar to image data 202 of FIG. 2A and may include still frame images and/or video clips. At optional block 404, computer-executable instructions stored on a memory of a device, such as a server, may be executed to preprocess the image data (e.g., to focus, resize, and/or crop the image data) as described with respect to preprocessor 210 and preprocessed image data 212 of FIG. 2A. Additionally, or alternatively, at block 404, spatial, temporal, and/or spatiotemporal filters may be used to remove noise.

At optional block 406, computer-executable instructions stored on a memory of a device, such as a server, may be executed to determine sample image data, as described with respect to sampling generator 214 and sampled image data 216 of FIG. 2A. At optional block 408, computer-executable instructions stored on a memory of a device, such as a server, may be executed to create and train a spatial model. For example, an CNN may be trained for image processing, detection, and/or recognition using large sets of images. For example, images from daily life (e.g., cars, bikes, apples, etc.) may be used to train the CNN generally for image recognition.

Additionally, or alternatively, CNNs may be trained or fine-tuned using specific dataset corresponding to cardiovascular anatomy including with and/or without CHD and/or anomalies to ultimately recognize CHDs and/or cardiovascular anomalies in input image data. The network may be further trained to identify image views, angles, and/or orientations. For example, echocardiogram technicians may consistently generate standardized views, angles or certain anatomy and the CNN may be trained to recognize such views, angles, and/or orientations. It is understood that the images and data used for training purposes may be different and/or may come from patients different than the image data input into the trained CNNs.

At block 410, computer-executable instructions stored on a memory of a device, such as a server, may be executed to process image data using the trained spatial model. The processed image data may be the preprocessed and/or sampled imaged data. At block 412, computer-executable instructions stored on a memory of a device, such as a server, may be executed to generate a spatial output using the image data and the trained spatial model. The spatial output may be the same as or similar to spatial output 226 of FIG. 2A.

At block 414, computer-executable instructions stored on a memory of a device, such as a server, may be executed to determine optical flow data as described with respect to optical flow generator 218 and optical flow data 220 of FIG. 2A. It is understood that blocks 414-420 may be executed simultaneously or nearly simultaneously with blocks 406-412. At optional block 416, computer-executable instructions stored on a memory of a device, such as a server, may be executed to train a temporal model using image data similar to optional block 408. It is understood that optional block 416 and optional block 408 may occur simultaneously and/or that the spatial stream and the temporal stream may be trained together such that optional block 408 and optional block 416 may be the same step. Additionally, or alternatively, the temporal model may be trained using optical flow data to ultimately recognize CHDs and/or cardiovascular anomalies in optical flow data and/or to identify image views, angles, and/or orientations in the optical flow data.

At block 418, computer-executable instructions stored on a memory of a device, such as a server, may be executed to process optical flow data using the trained temporal model. At block 420, computer-executable instructions stored on a memory of a device, such as a server, may be executed to generate a temporal output using the optical flow data and the trained temporal model. The temporal output may be the same as or similar to temporal output 228 of FIG. 2A. At block 422, fusion may be performed on the temporal output and spatial output to determine a spatiotemporal output, as described with respect to fuser 230 and spatiotemporal output 232 of FIG. 2A.

Figure 5A:
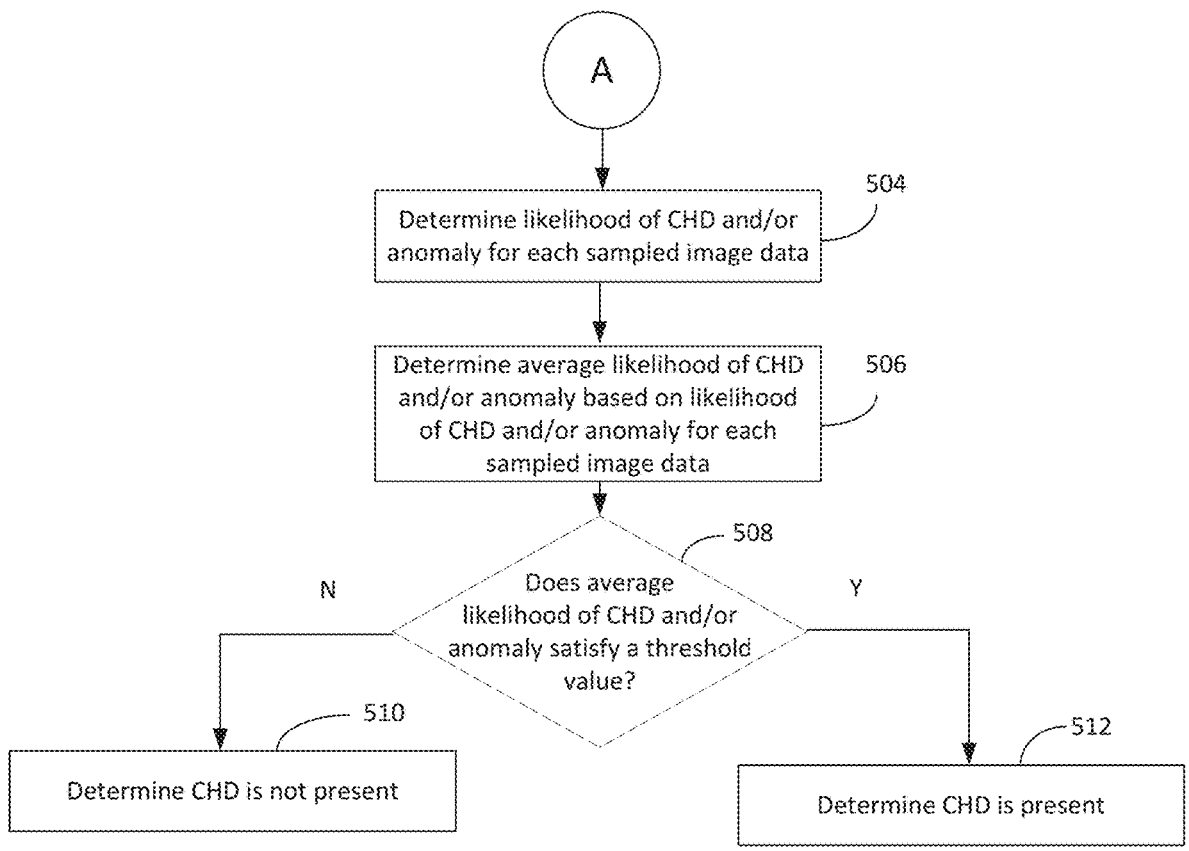
FIGS. 5A-5B illustrate process flows for determining whether CHDs and/or other cardiovascular anomalies is present based on a likelihood of a presence a CHD and/or other cardiovascular anomaly.
Figure 5B:
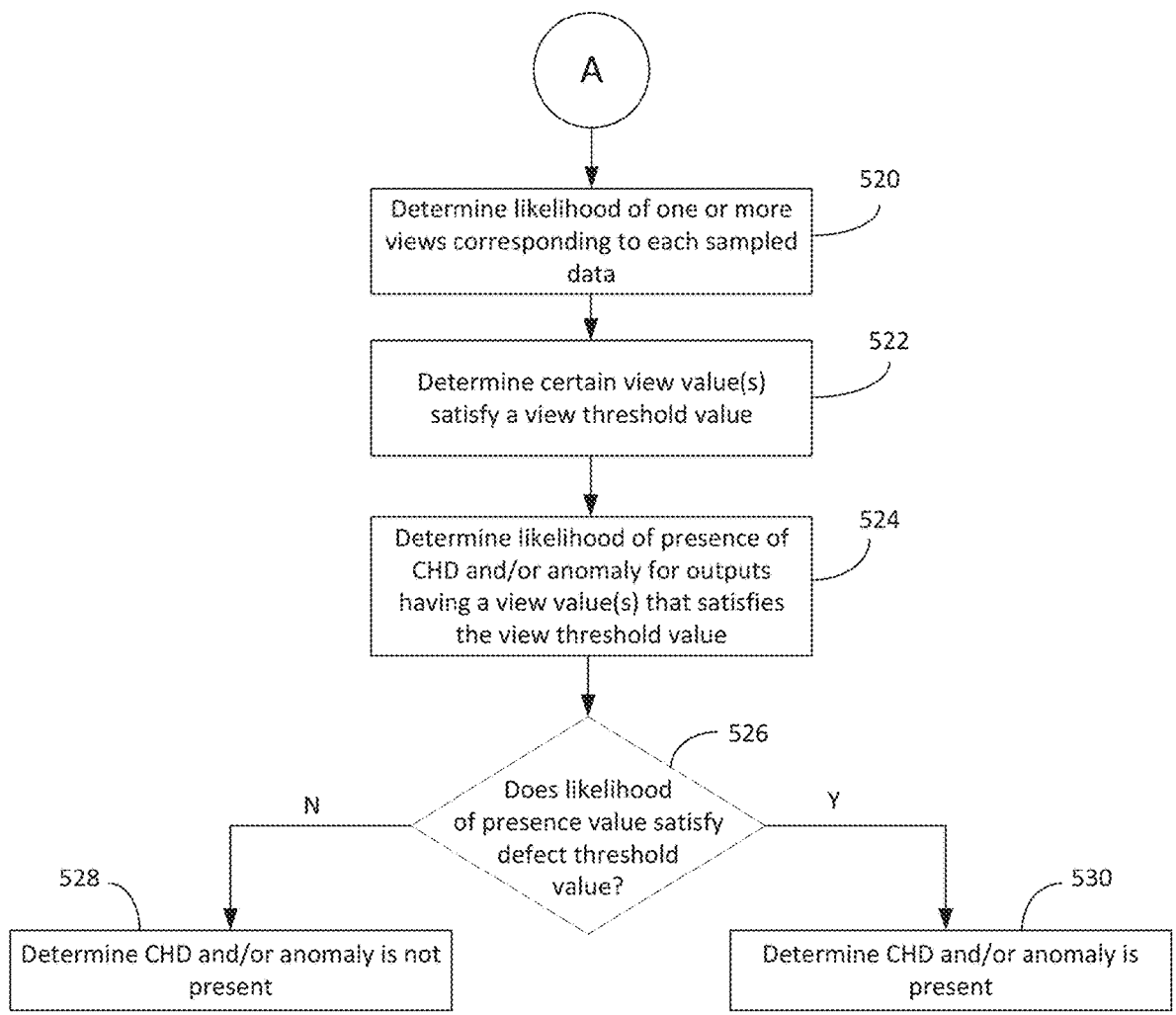

Referring now to FIGS. 5A and 5B, process flows are depicted for determining whether CHD and/or cardiovascular anomalies are present in the data flow. FIGS. 5A-5B may be initiated immediately following block 422 of FIG. 4. Some or all of the blocks of the process flows in this disclosure may be performed in a distributed manner across any number of devices (e.g., a server such as server 104 of FIG. 1, computing devices, imaging or sensor devices, or the like). Some or all of the operations of the process flow may be optional and may be performed in a different order.

Referring now to FIG. 5A, at block 504, computer-executable instructions stored on a memory of a device, such as a server, may be executed to determine a likelihood of one or more CHD and/or cardiovascular anomaly for each of the sampled image data and/or each frame or video clip input into the spatiotemporal CNN. For example, each output may include a likelihood of CHDs and/or cardiovascular anomalies and each output may correspond to a frame of image data and/or a video clip (e.g., multiple frames of image data).

At block 506, computer-executable instructions stored on a memory of a device, such as a server, may be executed to determine an average likelihood of CHDs and/or cardiovascular anomalies based on the likelihood of CHDs and/or cardiovascular anomalies for each sampled image data. For example, the likelihood of each CHD and/or cardiovascular anomaly in each output may be averaged. It is understood that other types of aggregation, modeling, and/or filtering calculations may alternatively or additionally be used other than the average calculation. For example, the system may determine the highest likelihood detected and may use that value for further processing and/or analysis. Alternatively, or additionally, key-points and/or contours of anatomy of the fetus may be determined.

At decision 508, computer-executable instructions stored on a memory of a device, such as a server, may be executed to compare the average likelihood of a CHD and/or cardiovascular anomaly to a threshold value. For example, the threshold value may be 51%, 75%, 90%, 99% or any other threshold value. If the threshold value is not satisfied by any average values (e.g., each average value is below the threshold value), at block 510 computer-executable instructions stored on a memory of a device, such as a server, may be executed to determine that no CHDs and/or cardiovascular anomalies are present.

Alternatively, if the threshold value is satisfied for one or more CHD and/or cardiovascular anomaly, at block 510 computer-executable instructions stored on a memory of a device, such as a server, may be executed to determine that the CHD and/or cardiovascular defect corresponding the average value that satisfies the threshold is present. For example, the spatiotemporal output may be a vector or matrix including several likelihood values between 0 and 1, each corresponding to a different CHD and/or cardiovascular anomaly and the values higher than the threshold value (e.g., 0.9) will be determined to be present. It may be desirable to set different threshold values for different abnormalities, conditions, morphological abnormalities, pathologies, and the like.

Referring now to FIG. 5B, an alternative or additional process flow for determining whether CHDs and/or cardiovascular anomalies are present in the image data is illustrated. At block 520, computer-executable instructions stored on a memory of a device, such as a server, may be executed to determine a likelihood of one or more views each corresponding to the sampled data and/or other image data input into the network. The view values may correspond to a likelihood of the presence of one or more views, angles, and/or orientations corresponding to each frame and/or video clip of the image data. For example, view values may be between 0-1.

At block 522, computer-executable instructions stored on a memory of a device, such as a server, may be executed to determine that certain view values satisfy a view threshold value. For example, the view threshold value could be any value such as 51%, 75%, 90%, 99%, etc. In one example, it may be determined that if the view value is greater than 0.9, there is high likelihood or confidence that the associated image data corresponds to a certain view.

At block 524, computer-executable instructions stored on a memory of a device, such as a server, may be executed to determine the likelihood of the presence of CHD and/or cardiovascular anomalies for outputs having view values satisfying the threshold value. Alternatively, or additionally, key-points and/or contours of anatomy of the fetus may be determined. At decision 526, computer-executable instructions stored on a memory of a device, such as a server, may be executed to compare each likelihood of CHD and/or cardiovascular anomaly corresponding to outputs with satisfied view threshold values to a defect threshold value. For example, the defect threshold value may be 51%, 75%, 90%, 99% or any other threshold value. If the threshold value is not satisfied by any average values (e.g., all average values are below the threshold value), at block 528 computer-executable instructions stored on a memory of a device, such as a server, may be executed to determine that no CHDs and/or cardiovascular anomalies are present.

If the defect threshold value is not satisfied by any values (e.g., all values are below the defect threshold value), at block 528 computer-executable instructions stored on a memory of a device, such as a server, may be executed to determine that CHD and/or cardiovascular anomalies are not present. Alternatively, if the defect threshold value is satisfied for one or more CHD and/or cardiovascular anomaly, at block 530 computer-executable instructions stored on a memory of a device, such as a server, may be executed to determine that the CHD and/or cardiovascular anomaly corresponding the value above the defect threshold value is present.

Figure 6:
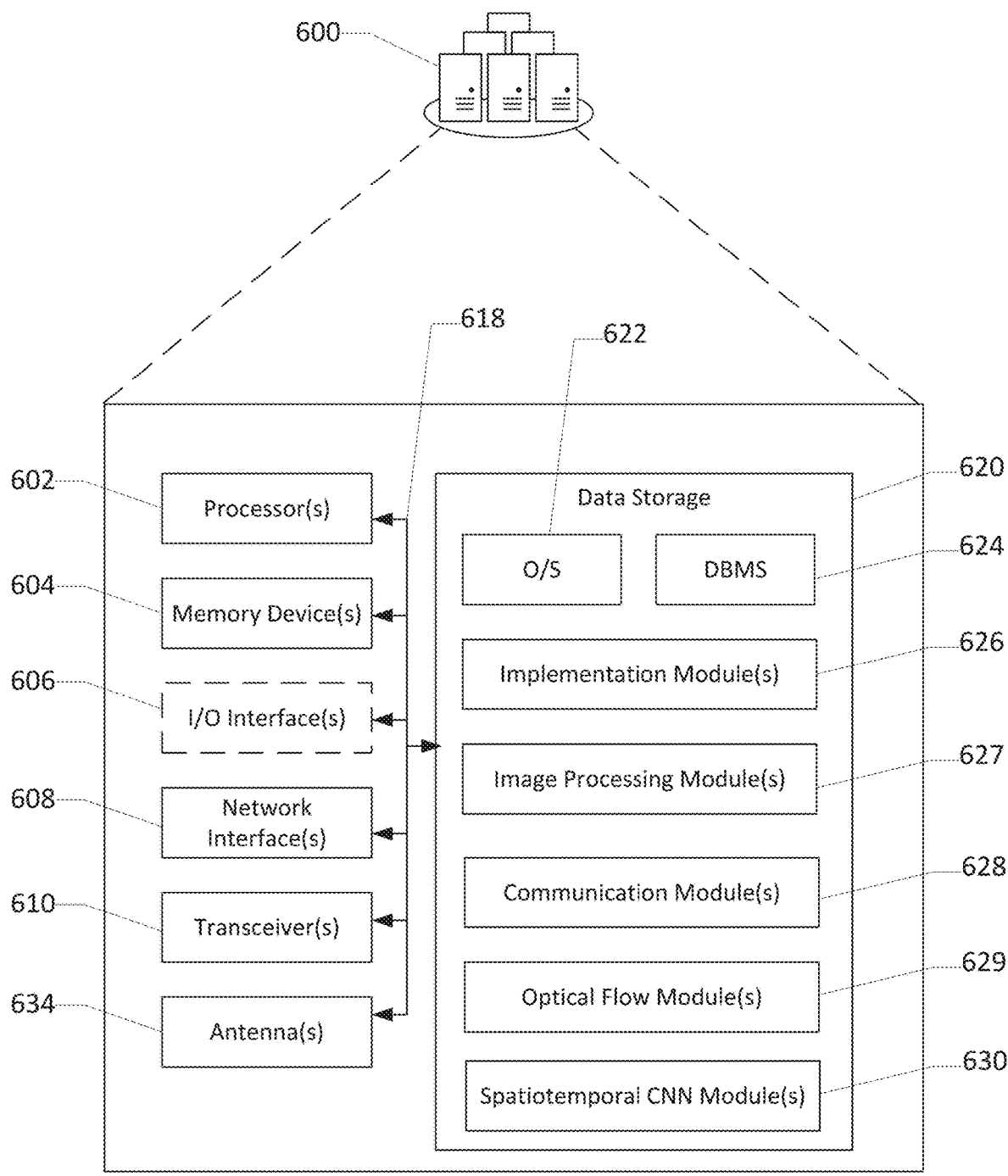
FIG. 6 is a schematic block diagram of a computing device, in accordance with one or more example embodiments of the disclosure.

Referring now to FIG. 6, a schematic block diagram of server 600 is illustrated. Server 600 may be the same or similar to server 104 of FIG. 1 or otherwise one or more of the servers of FIGS. 1-5B. It is understood that an imaging systems, analyst device and/or datastore may additionally or alternatively include one or more of the components illustrated in FIG. 6 and server 600 may alone or together with any of the foregoing perform one or more of the operations of server 600 described herein.

Server 600 may be designed to communicate with one or more servers, imaging systems, analyst devices, data stores, other systems, or the like. Server 600 may be designed to communicate via one or more networks. Such network(s) may include, but are not limited to, any one or more different types of communications networks such as, for example, cable networks, public networks (e.g., the Internet), private networks (e.g., frame-relay networks), wireless networks, cellular networks, telephone networks (e.g., a public switched telephone network), or any other suitable private or public packet-switched or circuit-switched networks.

In an illustrative configuration, server 600 may include one or more processors 602, one or more memory devices 604 (also referred to herein as memory 604), one or more input/output (I/O) interface(s) 606, one or more network interface(s) 608, one or more transceiver(s) 610, one or more antenna(s) 634, and data storage 620. The server 600 may further include one or more bus(es) 618 that functionally couple various components of the server 600.

The bus(es) 618 may include at least one of a system bus, a memory bus, an address bus, or a message bus, and may permit exchange of information (e.g., data (including computer-executable code), signaling, etc.) between various components of the server 600. The bus(es) 618 may include, without limitation, a memory bus or a memory controller, a peripheral bus, an accelerated graphics port, and so forth. The bus(es) 618 may be associated with any suitable bus architecture.

The memory 604 may include volatile memory (memory that maintains its state when supplied with power) such as random access memory (RAM) and/or non-volatile memory (memory that maintains its state even when not supplied with power) such as read-only memory (ROM), flash memory, ferroelectric RAM (FRAM), and so forth. Persistent data storage, as that term is used herein, may include non-volatile memory. In various implementations, the memory 604 may include multiple different types of memory such as various types of static random access memory (SRAM), various types of dynamic random access memory (DRAM), various types of unalterable ROM, and/or writeable variants of ROM such as electrically erasable programmable read-only memory (EEPROM), flash memory, and so forth.

The data storage 620 may include removable storage and/or non-removable storage including, but not limited to, magnetic storage, optical disk storage, and/or tape storage. The data storage 620 may provide non-volatile storage of computer-executable instructions and other data. The memory 604 and the data storage 620, removable and/or non-removable, are examples of computer-readable storage media (CRSM) as that term is used herein. The data storage 620 may store computer-executable code, instructions, or the like that may be loadable into the memory 604 and executable by the processor(s) 602 to cause the processor(s) 602 to perform or initiate various operations. The data storage 620 may additionally store data that may be copied to memory 604 for use by the processor(s) 602 during the execution of the computer-executable instructions. Moreover, output data generated as a result of execution of the computer-executable instructions by the processor(s) 602 may be stored initially in memory 604, and may ultimately be copied to data storage 620 for non-volatile storage.

The data storage 620 may store one or more operating systems (O/S) 622; one or more optional database management systems (DBMS) 624; and one or more program module(s), applications, engines, computer-executable code, scripts, or the like such as, for example, one or more implementation modules 626, image processing module 627, communication modules 628, optical flow module 629, and/or spatiotemporal CNN module. Some or all of these modules may be sub-modules. Any of the components depicted as being stored in data storage 620 may include any combination of software, firmware, and/or hardware. The software and/or firmware may include computer-executable code, instructions, or the like that may be loaded into the memory 604 for execution by one or more of the processor(s) 602. Any of the components depicted as being stored in data storage 620 may support functionality described in reference to correspondingly named components earlier in this disclosure.

Referring now to other illustrative components depicted as being stored in the data storage 620, the O/S 622 may be loaded from the data storage 620 into the memory 604 and may provide an interface between other application software executing on the server 600 and hardware resources of the server 600. More specifically, the O/S 622 may include a set of computer-executable instructions for managing hardware resources of the server 600 and for providing common services to other application programs (e.g., managing memory allocation among various application programs). In certain example embodiments, the O/S 622 may control execution of the other program module(s) for content rendering. The O/S 622 may include any operating system now known or which may be developed in the future including, but not limited to, any server operating system, any mainframe operating system, or any other proprietary or non-proprietary operating system.

The optional DBMS 624 may be loaded into the memory 604 and may support functionality for accessing, retrieving, storing, and/or manipulating data stored in the memory 604 and/or data stored in the data storage 620. The DBMS 624 may use any of a variety of database models (e.g., relational model, object model, etc.) and may support any of a variety of query languages. The DBMS 624 may access data represented in one or more data schemas and stored in any suitable data repository including, but not limited to, databases (e.g., relational, object-oriented, etc.), file systems, flat files, distributed datastores in which data is stored on more than one node of a computer network, peer-to-peer network datastores, or the like.

The optional input/output (I/O) interface(s) 606 may facilitate the receipt of input information by the server 600 from one or more I/O devices as well as the output of information from the server 600 to the one or more I/O devices. The I/O devices may include any of a variety of components such as a display or display screen having a touch surface or touchscreen; an audio output device for producing sound, such as a speaker; an audio capture device, such as a microphone; an image and/or video capture device, such as a camera; and so forth. Any of these components may be integrated into the server 600 or may be separate.

The server 600 may further include one or more network interface(s) 608 via which the server 600 may communicate with any of a variety of other systems, platforms, networks, devices, and so forth. The network interface(s) 608 may enable communication, for example, with one or more wireless routers, one or more host servers, one or more web servers, and the like via one or more of networks.

The antenna(s) 634 may include any suitable type of antenna depending, for example, on the communications protocols used to transmit or receive signals via the antenna(s) 634. Non-limiting examples of suitable antennas may include directional antennas, non-directional antennas, dipole antennas, folded dipole antennas, patch antennas, multiple-input multiple-output (MIMO) antennas, or the like. The antenna(s) 634 may be communicatively coupled to one or more transceivers 612 or radio components to which or from which signals may be transmitted or received. Antenna(s) 634 may include, without limitation, a cellular antenna for transmitting or receiving signals to/from a cellular network infrastructure, an antenna for transmitting or receiving Wi-Fi signals to/from an access point (AP), a Global Navigation Satellite System (GNSS) antenna for receiving GNSS signals from a GNSS satellite, a Bluetooth antenna for transmitting or receiving Bluetooth signals including BLE signals, a Near Field Communication (NFC) antenna for transmitting or receiving NFC signals, a 900 MHz antenna, and so forth.

The transceiver(s) 612 may include any suitable radio component(s) for, in cooperation with the antenna(s) 634, transmitting or receiving radio frequency (RF) signals in the bandwidth and/or channels corresponding to the communications protocols utilized by the server 600 to communicate with other devices. The transceiver(s) 612 may include hardware, software, and/or firmware for modulating, transmitting, or receiving—potentially in cooperation with any of antenna(s) 634—communications signals according to any of the communications protocols discussed above including, but not limited to, one or more Wi-Fi and/or Wi-Fi direct protocols, as standardized by the IEEE 802.11 standards, one or more non-Wi-Fi protocols, or one or more cellular communications protocols or standards. The transceiver(s) 612 may further include hardware, firmware, or software for receiving GNSS signals. The transceiver(s) 612 may include any known receiver and baseband suitable for communicating via the communications protocols utilized by the server 600. The transceiver(s) 612 may further include a low noise amplifier (LNA), additional signal amplifiers, an analog-to-digital (A/D) converter, one or more buffers, a digital baseband, or the like.

Referring now to functionality supported by the various program module(s) depicted in FIG. 6, the implementation module(s) 626 may include computer-executable instructions, code, or the like that responsive to execution by one or more of the processor(s) 602 may perform functions including, but not limited to, overseeing coordination and interaction between one or more modules and computer executable instructions in data storage 620, determining user selected actions and tasks, determining actions associated with user interactions, determining actions associated with user input, initiating commands locally or at remote devices, and the like.

The imaging processing module(s) 627 may include computer-executable instructions, code, or the like that responsive to execution by one or more of the processor(s) 602 may perform functions including, but not limited to, analyzing and processing image data (e.g., still frames and/or video clips) and cropping, segmenting, parsing, sampling, resizing, and/or altering the same.

The communication module(s) 628 may include computer-executable instructions, code, or the like that responsive to execution by one or more of the processor(s) 602 may perform functions including, but not limited to, communicating with one or more devices, for example, via wired or wireless communication, communicating with servers (e.g., remote servers), communicating with datastores and/or databases, communicating with imaging systems and/or analyst devices, sending or receiving notifications or commands/directives, communicating with cache memory data, communicating with computing devices, and the like.

The optical flow module(s) 629 may include computer-executable instructions, code, or the like that responsive to execution by one or more of the processor(s) 602 may perform functions including, but not limited to, generating optical flow data, including horizontal and vertical optical flow data, optical flow plots and/or representations, and other optical flow information from image data.

The spatiotemporal CNN module(s) 630 may include computer-executable instructions, code, or the like that responsive to execution by one or more of the processor(s) 602 may perform functions including, but not limited to, generating, running, and executing one or more spatiotemporal CNNs including one or more spatial CNN and one or more temporal CNN.

Although specific embodiments of the disclosure have been described, one of ordinary skill in the art will recognize that numerous other modifications and alternative embodiments are within the scope of the disclosure. For example, any of the functionality and/or processing capabilities described with respect to a particular device or component may be performed by any other device or component. Further, while various illustrative implementations and architectures have been described in accordance with embodiments of the disclosure, one of ordinary skill in the art will appreciate that numerous other modifications to the illustrative implementations and architectures described herein are also within the scope of this disclosure.

Certain aspects of the disclosure are described above with reference to block and flow diagrams of systems, methods, apparatuses, and/or computer program products according to example embodiments. It will be understood that one or more blocks of the block diagrams and flow diagrams, and combinations of blocks in the block diagrams and the flow diagrams, respectively, may be implemented by execution of computer-executable program instructions. Likewise, some blocks of the block diagrams and flow diagrams may not necessarily need to be performed in the order presented, or may not necessarily need to be performed at all, according to some embodiments. Further, additional components and/or operations beyond those depicted in blocks of the block and/or flow diagrams may be present in certain embodiments.

Accordingly, blocks of the block diagrams and flow diagrams support combinations of means for performing the specified functions, combinations of elements or steps for performing the specified functions, and program instruction means for performing the specified functions. It will also be understood that each block of the block diagrams and flow diagrams, and combinations of blocks in the block diagrams and flow diagrams, may be implemented by special-purpose, hardware-based computer systems that perform the specified functions, elements or steps, or combinations of special-purpose hardware and computer instructions.

Program module(s), applications, or the like disclosed herein may include one or more software components, including, for example, software objects, methods, data structures, or the like. Each such software component may include computer-executable instructions that, responsive to execution, cause at least a portion of the functionality described herein (e.g., one or more operations of the illustrative methods described herein) to be performed.

A software component may be coded in any of a variety of programming languages. An illustrative programming language may be a lower-level programming language such as an assembly language associated with a particular hardware architecture and/or operating system platform. A software component including assembly language instructions may require conversion into executable machine code by an assembler prior to execution by the hardware architecture and/or platform.

Another example programming language may be a higher-level programming language that may be portable across multiple architectures. A software component including higher-level programming language instructions may require conversion to an intermediate representation by an interpreter or a compiler prior to execution.

Other examples of programming languages include, but are not limited to, a macro language, a shell or command language, a job control language, a script language, a database query or search language, or a report writing language. In one or more example embodiments, a software component including instructions in one of the foregoing examples of programming languages may be executed directly by an operating system or other software component without having to be first transformed into another form.

A software component may be stored as a file or other data storage construct. Software components of a similar type or functionally related may be stored together such as, for example, in a particular directory, folder, or library. Software components may be static (e.g., pre-established or fixed) or dynamic (e.g., created or modified at the time of execution).

Software components may invoke or be invoked by other software components through any of a wide variety of mechanisms. Invoked or invoking software components may include other custom-developed application software, operating system functionality (e.g., device drivers, data storage (e.g., file management) routines, other common routines and services, etc.), or third-party software components (e.g., middleware, encryption, or other security software, database management software, file transfer or other network communication software, mathematical or statistical software, image processing software, and format translation software).

Software components associated with a particular solution or system may reside and be executed on a single platform or may be distributed across multiple platforms. The multiple platforms may be associated with more than one hardware vendor, underlying chip technology, or operating system. Furthermore, software components associated with a particular solution or system may be initially written in one or more programming languages, but may invoke software components written in another programming language.

Computer-executable program instructions may be loaded onto a special-purpose computer or other particular machine, a processor, or other programmable data processing apparatus to produce a particular machine, such that execution of the instructions on the computer, processor, or other programmable data processing apparatus causes one or more functions or operations specified in the flow diagrams to be performed. These computer program instructions may also be stored in a computer-readable storage medium (CRSM) that upon execution may direct a computer or other programmable data processing apparatus to function in a particular manner, such that the instructions stored in the computer-readable storage medium produce an article of manufacture including instruction means that implement one or more functions or operations specified in the flow diagrams. The computer program instructions may also be loaded onto a computer or other programmable data processing apparatus to cause a series of operational elements or steps to be performed on the computer or other programmable apparatus to produce a computer-implemented process.

Additional types of CRSM that may be present in any of the devices described herein may include, but are not limited to, programmable random access memory (PRAM), SRAM, DRAM, RAM, ROM, electrically erasable programmable read-only memory (EEPROM), flash memory or other memory technology, compact disc read-only memory (CD-ROM), digital versatile disc (DVD) or other optical storage, magnetic cassettes, magnetic tape, magnetic disk storage or other magnetic storage devices, or any other medium which can be used to store the information and which can be accessed. Combinations of any of the above are also included within the scope of CRSM. Alternatively, computer-readable communication media (CRCM) may include computer-readable instructions, program module(s), or other data transmitted within a data signal, such as a carrier wave, or other transmission. However, as used herein, CRSM does not include CRCM.

Although embodiments have been described in language specific to structural features and/or methodological acts, it is to be understood that the disclosure is not necessarily limited to the specific features or acts described. Rather, the specific features and acts are disclosed as illustrative forms of implementing the embodiments. Conditional language, such as, among others, "can," "could," "might," or "may," unless specifically stated otherwise, or otherwise understood within the context as used, is generally intended to convey that certain embodiments could include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

It should be understood that any of the computer operations described herein above may be implemented at least in part as computer-readable instructions stored on a computer-readable memory. It will of course be understood that the embodiments described herein are illustrative, and components may be arranged, substituted, combined, and designed in a wide variety of different configurations, all of which are contemplated and fall within the scope of this disclosure.

The foregoing description of illustrative embodiments has been presented for purposes of illustration and of description. It is not intended to be exhaustive or limiting with respect to the precise form disclosed, and modifications and variations are possible in light of the above teachings or may be acquired from practice of the disclosed embodiments. It is intended that the scope of the invention be defined by the claims appended hereto and their equivalents.

What is claimed is:

1. A method for determining a presence of one or more congenital heart defects (CHDs) in a fetus during pregnancy, the method comprising:
   determining, by a computing device, image data representative of a portion of the fetus's cardiovascular system, the image data comprising a series of image frames;
   processing the image data using an optical flow generator to generate optical flow data, the optical flow data indicative of movement of the image data between each frame of the series of image frames;
   determining a neural network system comprising a spatial model trained to process the image data and a temporal model trained to process the optical flow data corresponding to the image data;
   determining a spatial output using the spatial model and based on the image data, the spatial output corresponding to a first likelihood of a presence of one or more CHDs of the fetus, the spatial output comprising a matrix of values indicative of a presence of one or more standard view orientations in a respective image frame of the series of image frames;
   determining a temporal output using the temporal model and based on the optical flow data, the temporal output corresponding to a second likelihood of the presence one or more CHD of the patient;
   determining a third likelihood of the presence of one or more CHDs of the patient based on the spatial output and the temporal output; and
   causing a first device to display a user interface corresponding to the third likelihood of the presence of one or more CHDs.

2. The method of claim 1, wherein the third likelihood of the presence of one or more CHD of the patient comprises one or more of a likelihood of a presence of overriding artery, septal defect at cardiac crux, parallel great arteries, enlarged cardiothoracic ratio, right ventricular to left ventricular size discrepancy, tricuspid valve to mitral valve annular size discrepancy, pulmonary valve to aortic valve annular size discrepancy, abnormal outflow tracts relationship, cardiac axis deviation, atrial septal defect, atrioventricular septal defect, coarctation of the aorta, double-outlet right ventricle, d-transposition of the great arteries, Ebstein anomaly, hypoplastic left heart syndrome, interrupted aortic arch, ventricular disproportion, abnormal heart size, ventricular septal defect, abnormal atrioventricular junction, abnormal area behind the left atrium, abnormal left ventricle junction, abnormal aorta junction, abnormal right ventricle junction, abnormal pulmonary artery junction, arterial size discrepancy, right aortic arch abnormality, abnormal size of pulmonary artery, abnormal size of transverse aortic arch, or abnormal size of superior vena cava.

3. The method of claim 1, further comprising:
   comparing the third likelihood of the presence of one or more CHDs to a threshold value;
   determining the third likelihood of the presence of one or more CHDs satisfies the threshold value; and
   determining the presence of the one or more CHDs of the patient based on the third likelihood of the presence of one or more CHDs satisfying the threshold value.

4. The method of claim 1, further comprising:
   determining a request from the first device to generate a report corresponding to the third likelihood of the presence of one or more CHDs; and
   causing the first device to generate the report corresponding to the third likelihood of the presence of one or more CHDs.

5. The method of claim 1, further comprising training the spatial model and the temporal model using a plurality of second image data different from the image data.

6. The method of claim 1, further comprising removing at least a portion of the image data from each of the image frames in the series of image frames.

7. The method of claim 1, further comprising receiving the image data from an imaging system.

8. The method of claim 7, wherein the imaging system comprises an ultrasound or echocardiogram device.

9. The method of claim 8, wherein the image data comprises a first series of image frames corresponding to a first orientation of the ultrasound device or echocardiogram device and a second series of image frame corresponding to a second orientation of the ultrasound device or echocardiogram device.

10. The method of claim 1, further comprising sampling the image data such that only non-adjacent image frames in the series of image frames are processed by the spatial model.

11. The method of claim 1, wherein one or more of the spatial output is indicative of one or more of key-point data or contour data.

12. The method of claim 1, wherein one or more of the temporal output is indicative of one or more of key-point data or contour data.

13. The method of claim 1, further comprising determining one or more of key-point data or contour data based on the spatial output and the temporal output.

14. The method of claim 13, further comprising causing the first device to further display the one or more of key-point data or contour data.

15. A system for determining a presence of one or more congenital heart defects (CHDs) in a fetus during pregnancy, the system comprising,
   memory configured to store computer-executable instructions; and
   at least one computer processor configured to access memory and execute the computer-executable instructions to:
      determine, by a computing device, image data representative of a portion of the fetus's cardiovascular system, the image data comprising a series of image frames;
      process the image data using an optical flow generator to generate optical flow data, the optical flow data indicative of movement of the image data between each frame of the series of image frames;

determine a neural network system comprising a spatial model trained to process the image data and a temporal model trained to process the optical flow data corresponding to the image data;

determine a spatial output using the spatial model and based on the image data, the spatial output corresponding to a first likelihood of a presence of one or more CHDs of the fetus, the spatial output comprising a matrix of values indicative of a presence of one or more standard view orientation in a respective image frame of the series of image frames;

determine a temporal output using the temporal model and based on the optical flow data, the temporal output corresponding to a second likelihood of the presence one or more CHD of the patient;

determine a third likelihood of the presence of one or more CHDs of the patient based on the spatial output and the temporal output; and cause a first device to display a user interface corresponding to the third likelihood of the presence of one or more CHDs.

16. The system of claim 15, wherein the third likelihood of the presence of one or more CHDs of the patient comprises one or more of a likelihood of a presence of overriding artery, septal defect at cardiac crux, parallel great arteries, enlarged cardiothoracic ratio, right ventricular to left ventricular size discrepancy, tricuspid valve to mitral valve annular size discrepancy, pulmonary valve to aortic valve annular size discrepancy, abnormal outflow tracts relationship, cardiac axis deviation, atrial septal defect, atrioventricular septal defect, coarctation of the aorta, double-outlet right ventricle, d-transposition of the great arteries, Ebstein anomaly, hypoplastic left heart syndrome, interrupted aortic arch, ventricular disproportion, abnormal heart size, ventricular septal defect, abnormal atrioventricular junction, abnormal area behind the left atrium, abnormal left ventricle junction, abnormal aorta junction, abnormal right ventricle junction, abnormal pulmonary artery junction, arterial size discrepancy, right aortic arch abnormality, abnormal size of pulmonary artery, abnormal size of transverse aortic arch, or abnormal size of superior vena cava.

17. The system of claim 15, wherein the computer processor is further configured to execute the computer-executable instructions to:
compare the third likelihood of the presence of one or more CHDs to a threshold value;
determine the third likelihood of the presence of one or more CHDs satisfies the threshold value; and
determine the presence of the one or more CHDs of the patient based on the third likelihood of the presence of one or more CHDs satisfying the threshold value.

18. The system of claim 15, wherein the computer processor is further configured to execute the computer-executable instructions to:
determine a request from a first device to generate a report corresponding to the third likelihood of the presence of one or more CHDs;
cause the first device to generate the report corresponding to the third likelihood of the presence of one or more CHDs.

19. The system of claim 15, wherein the computer processor is further configured to execute the computer-executable instructions to train the spatial model and the temporal model using a plurality of second image data different from the first image data.

20. The system of claim 15, wherein the computer processor is further configured to execute the computer-executable instructions to remove at least a portion of the image data from each of the image frames in the series of image frames.

21. The system of claim 15, wherein the computer processor is further configured to execute the computer-executable instructions to receive the first image data from an imaging system.

22. The system of claim 21, wherein the imaging system comprises an ultrasound or echocardiogram device.

23. The system of claim 22, wherein the image data comprises a first series of image frames corresponding to a first orientation of the ultrasound device or echocardiogram device and a second series of image frames corresponding to a second orientation of the ultrasound device or echocardiogram device.

24. The system of claim 15, wherein the computer processor is further configured to execute the computer-executable instructions to sample the image data such that only non-adjacent image frames in the series of image frames are processed by the spatial model.

25. The system of claim 15, wherein one or more of the spatial output is indicative of one or more of key-point data or contour data.

26. The system of claim 15, wherein one or more of the temporal output is indicative of one or more of key-point data or contour data.

27. The system of claim 15, wherein the computer processor is further configured to execute the computer-executable instructions to determine one or more of key-point data or contour data based on the spatial output and the temporal output.

28. The system of claim 27, wherein the computer processor is further configured to execute the computer-executable instructions to cause the first device to further display the one or more of key-point data or contour data.

* * * * *